(12) United States Patent
Atkins et al.

(10) Patent No.: US 11,807,537 B2
(45) Date of Patent: Nov. 7, 2023

(54) METHODS FOR PRODUCING CARBON FIBER FROM COAL

(71) Applicant: CARBON HOLDINGS INTELLECTUAL PROPERTIES, LLC, Sheridan, WY (US)

(72) Inventors: Charles Agee Atkins, Sheridan, WY (US); Garrett W. Lindemann, Buffalo, WY (US); Matthew Targett, Sheridan, WY (US)

(73) Assignee: CARBON HOLDINGS INTELLECTUAL PROPERTIES, LLC, Ranchester, WY (US)

( * ) Notice: Subject to any disclaimer, the term of this patent is extended or adjusted under 35 U.S.C. 154(b) by 0 days.

(21) Appl. No.: 17/397,872

(22) Filed: Aug. 9, 2021

(65) Prior Publication Data

US 2021/0363018 A1  Nov. 25, 2021

Related U.S. Application Data

(63) Continuation of application No. 16/230,502, filed on Dec. 21, 2018, now Pat. No. 11,104,581.

(60) Provisional application No. 62/610,037, filed on Dec. 22, 2017.

(51) Int. Cl.

| | |
|---|---|
| *C01B 32/336* | (2017.01) |
| *C01B 32/184* | (2017.01) |
| *C01B 32/50* | (2017.01) |
| *C01B 32/30* | (2017.01) |
| *C01B 32/182* | (2017.01) |
| *C01B 32/158* | (2017.01) |
| *C01B 32/205* | (2017.01) |
| *C08F 6/28* | (2006.01) |
| *C08F 10/02* | (2006.01) |
| *C08F 20/44* | (2006.01) |
| *C10G 1/00* | (2006.01) |
| *C10G 1/02* | (2006.01) |
| *C01B 3/02* | (2006.01) |
| *G01N 33/22* | (2006.01) |
| *C10C 3/00* | (2006.01) |
| *D01F 9/12* | (2006.01) |
| *C01B 32/20* | (2017.01) |
| *C10B 53/04* | (2006.01) |
| *C01B 32/05* | (2017.01) |
| *C01B 32/154* | (2017.01) |
| *C01B 32/16* | (2017.01) |
| *C10B 53/00* | (2006.01) |
| *C10B 57/08* | (2006.01) |
| *D01F 9/15* | (2006.01) |
| *C08F 10/06* | (2006.01) |
| *C10G 1/04* | (2006.01) |
| *C10G 17/02* | (2006.01) |
| *C10G 27/12* | (2006.01) |

(52) U.S. Cl.
CPC .............. *C01B 32/336* (2017.08); *C01B 3/02* (2013.01); *C01B 32/05* (2017.08); *C01B 32/154* (2017.08); *C01B 32/158* (2017.08); *C01B 32/16* (2017.08); *C01B 32/182* (2017.08); *C01B 32/184* (2017.08); *C01B 32/20* (2017.08); *C01B 32/205* (2017.08); *C01B 32/30* (2017.08); *C01B 32/50* (2017.08); *C08F 6/28* (2013.01); *C08F 10/02* (2013.01); *C08F 10/06* (2013.01); *C08F 20/44* (2013.01); *C10B 53/00* (2013.01); *C10B 53/04* (2013.01); *C10B 57/08* (2013.01); *C10C 3/00* (2013.01); *C10C 3/002* (2013.01); *C10G 1/002* (2013.01); *C10G 1/02* (2013.01); *C10G 1/04* (2013.01); *D01F 9/12* (2013.01); *D01F 9/15* (2013.01); *G01N 33/222* (2013.01); *C10G 17/02* (2013.01); *C10G 27/12* (2013.01); *D10B 2101/12* (2013.01)

(58) Field of Classification Search
CPC .......... C08F 10/02; C08F 10/06; C08F 20/44; D01F 9/15; C01B 32/05; C01B 57/08; C10C 3/002
See application file for complete search history.

(56) References Cited

U.S. PATENT DOCUMENTS

| | | | |
|---|---|---|---|
| 2,581,575 A | 1/1952 | Broadman | |
| 2,624,698 A | 1/1953 | Hickey | |
| 3,639,953 A | 2/1972 | Kimura et al. | |
| 4,439,304 A | 3/1984 | Sudbury et al. | |
| 4,518,482 A | 5/1985 | Dickakian | |

(Continued)

FOREIGN PATENT DOCUMENTS

| | | |
|---|---|---|
| CN | 102392328 A | 3/2012 |
| CN | 103254921 A | 8/2013 |

(Continued)

OTHER PUBLICATIONS

Shi-Bin, Li, et al. "Study on Synthesis and Composite Properties of Condensed Polynuclear Aromatics Resin Using Coal Tar Pitch as Monomer and Trioxane as Cross-Linking Agent." Carbon, vol. 4, Dec. 15, 2008.

(Continued)

*Primary Examiner* — Robert D Harlan
(74) *Attorney, Agent, or Firm* — Dorsey & Whitney LLP

(57) ABSTRACT

A method of producing advanced carbon materials can include providing coal to a processing facility, beneficiating the coal to remove impurities from the coal, processing the beneficiated coal to produce a pitch, and treating the pitch to produce an advanced carbon material such as carbon fibers, carbon nanotubes, graphene, carbon fibers, polymers, biomaterials, or other carbon materials.

18 Claims, 8 Drawing Sheets

(56) References Cited

U.S. PATENT DOCUMENTS

| | | | |
|---|---|---|---|
| 4,597,858 | A | 7/1986 | Burgess et al. |
| 4,701,838 | A | 10/1987 | Swinkels et al. |
| 4,804,390 | A | 2/1989 | Lloyd et al. |
| 5,403,365 | A | 4/1995 | Merriam et al. |
| 5,692,807 | A | 12/1997 | Zimmerman |
| 6,771,368 | B1 | 8/2004 | Chadwick |
| 7,078,008 | B2 | 7/2006 | Allison et al. |
| 7,842,644 | B2 | 11/2010 | Kai et al. |
| 8,148,435 | B2 | 4/2012 | Fiato |
| 9,068,123 | B2 | 6/2015 | Kramer et al. |
| 9,074,138 | B2 * | 7/2015 | Rinker .................. C10B 57/08 |
| 9,181,509 | B2 | 11/2015 | Bland et al. |
| 9,938,150 | B2 | 4/2018 | Zhang et al. |
| 10,144,874 | B2 | 12/2018 | Walter et al. |
| 11,124,417 | B2 | 9/2021 | Atkins et al. |
| 2009/0038477 | A1 | 2/2009 | Abe et al. |
| 2009/0061193 | A1 | 3/2009 | Hara et al. |
| 2011/0011719 | A1 | 1/2011 | Rinker |
| 2012/0076703 | A1 * | 3/2012 | Stiller .................. C10B 57/04 422/187 |
| 2014/0120030 | A1 | 5/2014 | Kim et al. |
| 2014/0223882 | A1 | 8/2014 | Shah et al. |
| 2015/0141726 | A1 | 5/2015 | Thakkar et al. |
| 2016/0060122 | A1 | 3/2016 | Tour et al. |
| 2017/0080399 | A1 | 3/2017 | Johnson et al. |
| 2017/0198221 | A1 | 7/2017 | Targett et al. |
| 2017/0313886 | A1 | 11/2017 | Colyar et al. |
| 2018/0142158 | A1 | 5/2018 | Hamaguchi et al. |
| 2018/0155201 | A1 | 6/2018 | Zhang |
| 2019/0194022 | A1 | 6/2019 | Atkins et al. |
| 2019/0194025 | A1 | 6/2019 | Atkins et al. |
| 2019/0194364 | A1 | 6/2019 | Atkins et al. |
| 2019/0194544 | A1 | 6/2019 | Atkins et al. |
| 2019/0194828 | A1 | 6/2019 | Atkins et al. |

FOREIGN PATENT DOCUMENTS

| | | |
|---|---|---|
| CN | 104232130 A | 12/2014 |
| CN | 105819430 A | 8/2016 |
| CN | 105836739 A | 8/2016 |
| CN | 106498564 A | 3/2017 |
| CN | 107407012 A | 11/2017 |
| EP | 0118232 A1 | 9/1984 |
| JP | S58185682 A | 10/1983 |
| JP | S59-033384 A | 2/1984 |
| JP | S59174511 A | 10/1984 |
| JP | S6174660 A | 4/1986 |
| JP | H06287568 A | 10/1994 |
| JP | H09194849 A | 7/1997 |
| JP | 2016210925 A | 12/2016 |
| WO | 2015179806 A1 | 11/2015 |
| WO | 2016118214 A2 | 7/2016 |
| WO | 2016181929 A1 | 11/2016 |
| WO | 2019133539 A1 | 7/2019 |

OTHER PUBLICATIONS

Andresen, John M., et al. "Synthesis of pitch materials from hydrogenation of anthracite." Fuel processing technology 85.12 (2004): 1361-1372..

International Preliminary Report on Patentability received for International Application No. PCT/IB2018/067351, dated Jul. 2, 2020, 10 pages..

International Preliminary Report on Patentability Received for International Application No. PCT/US2018/067341, dated Jul. 2, 2020, 10 pages.

International Search Report and Written Opinion for PCT Application No. PCT/US2018/067341, dated May 23, 2019.

International Search Report and Written Opinion for PCT Application No. PCT/US2018/067351, dated May 2, 2019.

Li, Gang, et al. "One-step green synthesis of nitrogen and phosphorus co-doped pitch-based porous graphene-like carbon for supercapacitors." Journal of Porous Materials 24.6 (2017): 1689-1696..

IUPAC. Compendium of Chemical Terminology, 2nd ed. (the "Gold Book"). Compiled by A. D. McNaught and A. Wilkinson. Blackwell Scientific Publications, Oxford (1997)., Online version (2019-) created by S. J. Chalk. ISBN 0-9678550-9-8. https://doi.org/10.1351/goldbook..

Black, Sara , "Coal As an Avenue to Low-Cost Carbon Fibers", Black, Sara, Coal As an Avenue to Low-Cost Carbon Fibers, Oct. 18, 2017, Composite World; https://www.compositesworld.com/articles/coal-as-an-avenue-to-low-cost-carbon-fibers (Year: 2017), Oct. 18, 2017.

Kim, et al., "Pitch-Based Carbon Fibers From Coal Tar or Petroleum Residue Under the Same Processing Condition", Carbon Letters vol. 19, Jun. 14, 2016, 72-78.

Ye, Ruquan et al., "Bandgap engineering of coal-derived graphene quantum dots. (Supporting Information)" ASC applied materials & interfaces 7.12 (2015): S1-S5..

Wazir et al., Preparation of mesophase from coal tar pitch, 2003, New Carbon Materials, vol. 18, No. 4, pp. 281-285 (Year: 2003).

Extended European Search Report dated Sep. 10, 2021 for EP Application No. 18892070.6.

Sasikala, Suchithra Padmajan, et al. "High yield synthesis of aspect ratio controlled graphenic materials from anthracite coal in supercritical fluids." ACS nano 10.5 (2016); 5293-5303.

Wang, Lu et al. "Remarkable electrochemical properties of electrochemically reduced graphene oxide towards oxygen reduction reaction are caused by residual metal-based impurities." Electrochemistry Communications 62 (2016): 17-20.

Higgins, Drew C., et al., "Oxygen reduction on graphene-carbon nanotube composites doped sequentially with nitrogen and sulfur", Acs Catalysis 4.8 (2014): 2734-2740.

Wei, Qiliang, et al., "Nitrogen-doped carbon nanotube and graphene materials for oxygen reduction reactions", Catalysts 5.3 (2015): 1574-1602.

* cited by examiner

METHODS FOR PRODUCING CARBON FIBER FROM COAL

CROSS-REFERENCE TO RELATED APPLICATIONS

This is a continuation of U.S. application Ser. No. 16/230,502, filed 21 Dec. 2018, and entitled "METHODS FOR PRODUCING CARBON FIBERS FROM COAL," now U.S. Pat. No. 11,104,581 issued Aug. 31, 2021, which claims priority to U.S. Provisional Patent Application No. 62/610,037 filed on 22 Dec. 2017, titled "METHODS FOR PRODUCING ADVANCED CARBON MATERIALS FROM COAL," the disclosures of which is incorporated herein, by reference, in its entirety.

BACKGROUND

Coal is a highly varied heterogeneous material that has been mined and principally used for three purposes over thousands of years: 1) the generation of thermal heat and power generation through incineration, 2) the production of steel and other metals by coking, and 3) the production of what are now widely known as "petrochemicals" through pyrolysis or liquefaction. Despite the fact that coal has been extensively used for thousands of years, more than 99% of it has been incinerated to produce heat and power. This process is now widely known to produce a host of adverse environmental and economic effects.

Additional uses of coal has been the topic of research for many years. The basic chemistry of coal was well understood by at least the early twentieth century. Significant research was conducted with the aim of deriving liquid transportation fuels from coal in order to supplant petroleum. One notable breakthrough was the development of the Fischer-Tropsch process in Germany, around 1925, which converted gasified coal into liquid hydrocarbons. Additionally, Sasol, a major South African company, focused on the conversion of solid coal to liquid transportation fuels via catalytic cracking. Similarly, the United States Department of Energy sought to develop coal-based transportation fuels as an alternative to petroleum-based fuels. However, due to research driven petroleum technology and the decreasing costs of petroleum, the use of coal to produce liquid transportation fuels at large scales never became economically feasible.

Although significant research has been conducted on coal liquefaction and the use of coal to form other products for more than a century, the ability to produce high-value, high-performance carbon based products, such as carbon fibers, from coal remains an open question. In recent years, carbon-based technologies have come to the forefront, with rapid developments being made in in the commercialization of advanced carbon materials such as carbon fibers, resins, graphene, and carbon nanotubes. As these advanced materials are increasingly used in mass produced, high volume applications, there is a need to quickly and economically supply large quantities of advanced carbon materials to manufacturers. Thus, while improvements in the derivation of fuels and other products from coal are being explored, there remains significant work to be done in developing processes to convert coal into the advanced carbon materials that will be instrumental in the economy of the future.

SUMMARY

A method of producing an advanced carbon material includes providing an amount of coal to a processing facility, beneficiating the amount of coal at the processing facility to remove impurities therefrom, processing the beneficiated amount of coal at the processing facility to produce an amount of pitch from at least some of the amount of coal, and treating at least some of the amount of pitch at the processing facility to produce the advanced carbon material.

The method of producing an advanced carbon material can include providing coal to a processing facility by extracting coal from a coal mine.

The method of producing an advanced carbon material can include providing coal to a processing facility by extracting coal from the coal mine via a high wall coal mining process.

The method of producing an advanced carbon material can include transporting coal extracted from the coal mine to the processing facility.

The method of producing an advanced carbon material can include using raw coal as an initial material.

The method of producing an advanced carbon material can include heating the amount of coal to a first temperature for a first duration, and heating the amount of coal to a second, higher temperature for a second duration.

The method of producing an advanced carbon material can include removing impurities from the coal, such as mercury. Beneficiating the coal can remove at least 85% of mercury from the coal.

The method of producing an advanced carbon material can include removing water from the coal.

The method of producing an advanced carbon material can include beneficiating the coal to produce a beneficiated amount of coal having less than about 5 wt. % of water.

The method of producing an advanced carbon material can include removing volatile matter from the coal. Removal of at least 50% of the volatile matter can be removed from the coal.

The method of producing an advanced carbon material can include processing the beneficiated amount of coal at the processing facility to produce an amount of pitch from at least some of the amount of coal, including subjecting the beneficiated amount of coal to a pyrolysis process.

The method of producing an advanced carbon material can include processing the beneficiated amount of coal at the processing facility to produce an amount of pitch from at least some of the amount of coal, including subjecting the beneficiated amount of coal to a direct liquefaction process.

The method of producing an advanced carbon material can include processing the beneficiated amount of coal at the processing facility includes subjecting the beneficiated amount of coal to an indirect liquefaction process.

The method of producing an advanced carbon material can include processing the beneficiated amount of coal at the processing facility includes producing an amount of solid char.

The method of producing an advanced carbon material can include treating at least some solid char to produce an amount of activated carbon.

The method of producing an advanced carbon material can include processing the beneficiated amount of coal at the processing facility includes producing an amount of coal liquid extract.

The method of producing an advanced carbon material can include treating at least some of the coal liquid extract to produce an amount of benzene.

The method of producing an advanced carbon material can include treating at least some of the coal liquid extract to produce an amount of paraxylene.

The method of producing an advanced carbon material can include using pitch that comprises one of mesophase pitch, isotropic pitch, or mesophase pitch.

The method of producing an advanced carbon material can include spinning at least some of the amount of pitch to produce the advanced carbon material.

The method of producing an advanced carbon material can include forming advanced carbon materials including one or more of carbon fibers, carbon nanotubes, graphite, graphene, graphite nano-platelets, fullerenes, pyrolytic carbon, carbon foams, and resins.

The method of producing an advanced carbon material can include treating at least some of the amount of pitch at the processing facility including treating a first amount of pitch to form a first advanced carbon material and treating a second amount of pitch to form a second advanced carbon material.

The method of producing an advanced carbon material wherein the first advanced carbon material includes carbon fibers and the second advanced carbon material includes a polymer.

The method of producing an advanced carbon material can include combining the carbon fibers and the polymer to form a carbon fiber reinforced polymer.

According to some embodiments, a method of producing synthetic graphite from coal at a processing facility, can comprise providing coal to the processing facility, beneficiating the coal to remove a desired amount of impurities therefrom, and processing the beneficiated coal to produce synthetic graphite.

The synthetic graphite includes a desired amount of impurities. The impurities can include one or more of cadmium, selenium, or other metals. The method can further comprise processing the synthetic graphite to produce synthetic graphene. Processing the synthetic graphite to produce synthetic graphene can comprise exfoliation. The synthetic graphene can include a desired amount of impurities.

According to some embodiments, a synthetic graphite formed from pitch derived from coal is described herein. The synthetic graphite can further comprise a desired amount of one or more impurities found in coal.

According to some embodiments, a synthetic graphene formed from pitch derived from coal is described herein. The synthetic graphene can further comprise a desired amount of one or more impurities found in coal.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

Figure 1:
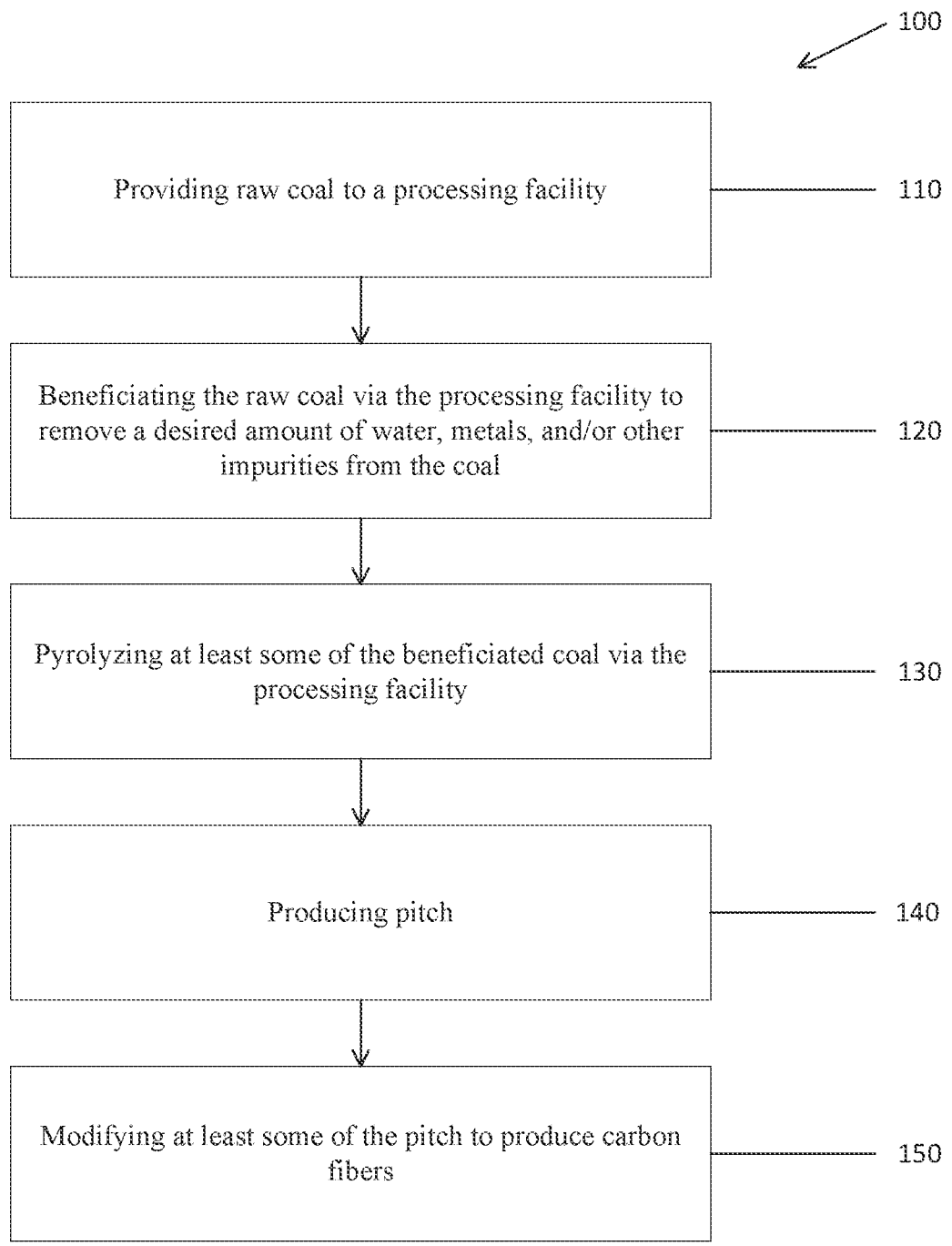
FIG. 1 is a flow chart of an example method 100 to form carbon fibers, according to an embodiment.

As described below, carbon fibers can be produced from raw, mined coal. In an embodiment, raw coal can be transported to a processing facility. The coal can then be beneficiated in order to remove a desired amount of impurities. The impurities (e.g., any compound or element other than carbon or hydrogen) removed from the coal can include at least one of mercury, arsenic, cadmium, other heavy metals, water, or volatile compounds. In some cases, beneficiation can include heating the coal to remove these impurities. The beneficiated coal can then be processed to produce pitch and, optionally, one or more additional advanced carbon materials (i.e., non-carbon fiber advanced carbon materials). The processing can include subjecting the beneficiated coal to a liquid extraction process (e.g., pyrolysis process, direct liquefaction process, indirect liquefaction process, or processing involving one or more membranes). In some cases, these processes disclosed herein can produce one or more byproducts (e.g., at least one of gases, solid char, or coal liquid extract) in addition to pitch which themselves can be processed to form useful materials, such as carbon fiber and additional advanced carbon materials. For example, solid char can be processed to form activated carbon, and coal liquid extracted can be processed to form aromatic compounds such as benzene and paraxylene.

In some embodiments, the pitch produced by the processes described herein can be an isotropic pitch, and can be converted to a mesophase pitch by processing as needed or desired. The pitch can then be treated and/or modified to produce the carbon fiber (e.g., the pitch can be spun to form carbon fibers), and, optionally, one or more additional advanced carbon materials (e.g., processed to form synthetic graphite, etc.). The carbon fiber and, optionally, the additional advanced carbon materials can be subjected to further processing, or can be delivered to third parties for use, for example in manufacturing. In some cases, the carbon fiber can be produced and combined to form secondary material, such as a resin or polymer to form a carbon fiber reinforced composite.

In some embodiments, one or more of the processes or process steps described herein can utilize or be carried out in the presence of one or more catalysts. For example, one or more process can include a hydrogenation catalyst. In some embodiments, the catalyst can comprise a metal (e.g., platinum). In some cases, the catalyst can be a multi-part catalyst (e.g., a catalyst comprising two or more metals). In some cases, a catalyst can include a ceramic or mineral material (e.g., a silicate material, such as an aluminosilicate material). In some cases, a catalyst can include any catalytic material now known or as can yet be discovered for use in processing coal.

In some embodiments, all of the beneficiation, processing, and treatment steps described herein can be performed at a single processing facility, for example a single processing plant or compound. However, in other embodiments, one or more steps can be performed at separate facilities and the products of each step can be stored and transported between each facility. As used herein, the term processing facility can refer to one or more laboratories, buildings, process flows, or other apparatuses at about the same geographic location. For example, a processing facility can comprise a single building or factory complex at a single geographic location which comprises such equipment to perform the processes and methods described herein.

In an embodiment, carbon fiber is the only advanced carbon material produced during the processes disclosed herein. In an embodiment, as previously discussed, the processes disclosed herein can form carbon fiber and one or more additional advanced carbon materials. In an example, the one or more additional advanced carbon materials can include, but are not limited to, resins (e.g., polyacrylonitrile, polyurethane resins, cyanate ester resins, epoxy resins, methacrylate resins, polyester resins, and other suitable resins), carbon foams, single-walled carbon nanotubes, multi-walled carbon nanotubes, carbon megatubes, graphite, graphene, graphite nano-platelets, nanoribbons, nanobuds, fullerenes (e.g., buckminsterfullerene and multi-cored fullerenes), quantum dots, activated carbon, and pyrolyzed carbon. In an example, the additional advanced carbon materials produced by the processes described herein can also include, but are not limited to polymers. In an example, the additional advanced carbon materials produced by the processes described herein can also include one or more materials that can be used as precursors in the formation of additional advanced carbon materials. Examples of the precursors can include at least one of alkanes, alkenes, or alkynes. In an example, the additional advanced carbon materials can comprise biologically useful materials or biopolymers (e.g., at least one of proteins, amino acids, nucleic acids, collagen, chitosan, or sugars).

Producing the carbon fiber and, optionally, the one or more additional advanced carbon materials from coal has several advantages over producing the carbon fiber and, optionally, the one or more additional advanced carbon materials from other carbon sources (e.g., oil). For example, the supply and price of oil is highly volatile which can affect the ability of manufacturers to obtain oil for the production of the carbon fibers and the additional advanced carbon materials. This, in turn, can cause shortages of the carbon fibers and the additional advanced carbon materials which can hamper manufacturer's ability to make devices, parts, etc. that include the carbon fiber and the additional advanced carbon materials. Additionally, producing the resin from coal produces at least one of resin, pitch, or one or more byproducts exhibiting a low hydrogen to carbon ratio (e.g., a hydrogen to carbon ratio of less than about 0.5, less than about 0.2, or less than about 0.1). The low hydrogen to carbon ratio can at least one improve the yield of resin formed from the coal, eliminate the need for an external source of hydrogen, or reduce the amount of carbon dioxide produced during the processes disclosed herein. Further, coal can include one or more impurities therein. The presence of the one or more impurities can affect the properties of the carbon fiber and the additional advanced carbon material. For instance, at least some of at least one of the impurities can intentionally and selectively not be removed from the coal during the beneficiation process or during another process. The impurity or impurities that are not removed from the coal can act as dopants in the carbon fiber and the one or more additional advance carbon materials which, in turn, can affect the properties of the carbon fiber and the one or more additional advanced carbon materials. As such, the impurities that are present in the coal and the ability to selectively remove the impurities from the coal can allow for a high degree of control over the composition and properties of the carbon fiber and the additional advanced carbon materials that are manufactured from coal. Further, the presence of the impurities in the coal result in less processing being required to form the carbon fiber and the additional advanced carbon materials. For example, the maintaining the impurity or impurities in the coal can at least one of simplify the beneficiation processes or other purification processes, facilitate the operation of one or more other non-beneficiation processes, or preclude the need for actively doping the coal, carbon fiber, or additional advanced carbon materials. Additionally, the carbon fibers formed from coal can exhibit higher graphene levels, are more elastic, and exhibit higher tensile strengths than carbon fiber formed from oil.

Methods of Forming the Carbon Fiber and Other Byproducts from Raw Coal

FIG. 1 is a flow chart of an example method 100 to form carbon fibers, according to an embodiment. The method 100 can include one or more of providing raw coal to a processing facility at block 110; beneficiating the raw coal via the processing facility at block 120 to remove a desired amount of water, metals, and/or other impurities from the coal; pyrolyzing at least some of the beneficiated coal via the processing facility at block 130; producing pitch at block 140; and modifying at least some of the pitch to produce carbon fibers at block 150. The carbon fibers can include a selected amount of a remainder of one or more impurities that were not removed during the method 100. The method 100 is only an example. As such, one or more blocks of the method 100 can be omitted, supplemented, combined, or divided. Further, the method 100 can include one or more additional acts, such as producing at least one byproduct from the coal (e.g., at least one of char, one or more gases, or one or more coal liquid extracts) or treating the pitch to produce one or more additional advanced carbon materials.

In some embodiments, the raw coal can be provided to a processing facility at block 110 by any method that is now known or that can be developed in the future. For example, coal is generally extracted from naturally occurring layers or veins, known as coal beds or coal seams, by mining. Coal can be extracted by surface mining, underground mining, or various other forms of mining. Typically, coal that has been extracted via mining, but has not been otherwise processed is referred to as raw coal. In some cases, the raw coal can be extracted via a surface mining process, such as a high wall mining process, strip mining process, or contour mining process. In some cases, the raw coal can be extracted via an underground mining process, such as by a longwall mining process, continuous mining process, blast mining process, retreat mining process, or room and pillar mining process.

The raw coal can be mined or extracted from a location relatively near to the processing facility. For example, the processing facility can be located at, or near a coal extraction area. However, in other cases coal can be extracted from any location and transported to the processing facility. In some cases raw coal can be provided to the processing facility as needed to produce a desired amount of advanced carbon materials. However, in some other cases, raw coal can be provided and stored at the processing facility until it is processed.

The coal provided in block 110 can be ranked or graded based on its contents and properties. Although a variety of coal classification schemes exist, a general metamorphic grade is used herein to generally describe raw coal. These grades are used generally to aid in the understanding of the present disclosure and are not intended to limit to types of coal which can be used to produce the carbon fiber and, optionally, the one or more additional advanced carbon materials as described herein. While certain classifications of coal can be preferable for use in the processes described herein, such processes are not strictly limited to the discussed classifications of coal, if any. In some embodiments, the coal utilized by the processes described herein can be lignite coal, and can have a volatile content of greater than about 45 wt. %. In some embodiments, the coal can be sub-bituminous coal, bituminous coal, and/or anthracite coal. In some embodiments, the coal can be coal extracted from the Brook Mine near Sheridan, Wyo. It is currently believed by the inventors that the composition of the coal extracted from the Brook Mine includes several impurities at beneficial concentrations that can facilitate the formation of carbon fiber exhibiting certain mechanical, chemical, and/or electrical properties, as discussed in more detail below. In some cases, the preferred coal for use in the processes described herein can be selected by the skilled artisan. For example, the preferred coal can be selected based one at least one of one or more destructive or non-destructive chemical analyzation techniques (e.g., Raman spectroscopy, energy dispersive x-ray spectroscopy, etc.) or one or more computing techniques. In some embodiments, the coal can exhibit an initial hydrogen to carbon ratio that is greater than about 0.7, such as in ranges 0.7 to about 1.0, about 0.7 to about 0.75, about 0.725 to about 0.0775, about 0.75 to about 0.8, about 0.0775 to about 0.85, about 0.8 to about 0.9, about 0.85 to about 0.95, or about 0.9 to about 1.0.

As previously discussed, the raw coal can be provided to a processing facility at block 110 for use in the method 100. The processing facility can have the capacity to store raw coal for use as needed, or can receive raw coal as needed to produce a desired amount of the carbon fiber. As is well known in the art, coal can be provided via truck, train, or any other form of transportation. Further, the processing facility can be situated at a coal extraction site, such that coal extraction site can be considered as part of the processing facility.

As previously discussed, the raw coal can include one or more impurities therein. The one or more impurities can include, but are not limited to volatile heavy metals (e.g., mercury, selenium, arsenic, and cadmium), alkali metals (e.g., sodium metals, potassium metals), heteroatoms (e.g., sulfur, oxygen, and halogens), silicon, aluminum, titanium, calcium, iron, magnesium, sodium, potassium, sulfur, strontium, barium, manganese, phosphorus, antimony, arsenic, barium, beryllium, boron, bromine, cadmium, chlorine, chromium, cobalt, copper, fluorine, lead, lithium, manganese, mercury, molybdenum, nickel, selenium, silver, strontium, thallium, tin, vanadium, zinc, and/or zirconium or oxides thereof. For example, depending on the impurity and the source of the raw coal, any of the impurities disclosed herein can form 0 weight percent ("wt. %") to about 25 wt. % of the raw coal, such as in ranges of about greater than 0 wt. % to about 0.001 wt. %, about 0.0005 wt. % to about 0.002 wt. %, about 0.001 wt. % to about 0.003 wt. %, about 0.002 wt. % to about 0.004 wt. %, about 0.003 wt. % to about 0.005 wt. %, about 0.004 wt. % to about 0.006 wt. %, about 0.005 wt. % to about 0.008 wt. %, about 0.007 wt. % to about 0.01 wt. %, about 0.009 wt. % to about 0.02 wt. %, about 0.01 wt. % to about 0.03 wt. %, about 0.02 wt. % to about 0.04 wt. %, about 0.03 wt. % to about 0.05 wt. %, about 0.04 wt. % to about 0.06 wt. %, about 0.05 wt. % to about 0.08 wt. %, about 0.07 wt. % to about 0.1 wt. %, about 0.09 wt. % to about 0.2 wt. %, about 0.1 wt. % to about 0.3 wt. %, about 0.2 wt. % to about 0.4 wt. %, about 0.3 wt. % to about 0.5 wt. %, about 0.4 wt. % to about 0.6 wt. %, about 0.5 wt. % to about 0.8 wt. %, about 0.7 wt. % to about 1 wt. %, about 0.9 wt. % to about 2 wt. %, about 1 wt. % to about 4 wt. %, about 3 wt. % to about 6 wt. %, about 5 wt. % to about 8 wt. %, about 7 wt. % to about 10 wt. %, about 9 wt. % to about 15 wt. %, or about 10 wt. % to about 25 wt. %.

At block 120, the raw coal can be beneficiated to remove at least some of at least one of the impurities that are present in the raw coal to form beneficiated coal (also known as upgraded coal), according to an embodiment. For example, the raw coal can be beneficiated to remove at least one water, heavy metals, volatile compounds, alkali metals, or heteroatoms from the raw coal, thereby producing the beneficiated coal. In an embodiment, the raw coal can be beneficiated to remove a significant portion of at least one of the impurities.

The beneficiation process can include heating the raw coal to one or more desired temperatures. The one or more desired temperature can be about 100° C. to about 500° C., such as in ranges of about 100° C. to about 290° C., 100° C. to about 150° C., about 125° C. to about 200° C., or about 150° C. to about 290° C. The temperature that the raw coal is heated to can be selected to selectively remove at least some of at least one of the impurities that are present in the raw coal. For example, the raw coal can be heated to a temperature of about 100° C. to about 150° C. to remove moisture from the raw coal and about 150° C. to about 290° C. to remove volatile metals from the raw coal. In some cases, the beneficiation process can comprise heating the raw coal to a first desired temperature. Heating the raw coal to the first desired temperature can remove one or more first impurities. In some embodiments, beneficiation can then include heating the raw coal to a second, higher desired temperature. Heating the raw coal to the second desired temperature can remove one or more second impurities.

The beneficiation process can include heating the raw coal to the desired temperature for a desired duration. The desired duration can be about 1 second to several days, such as in ranges of about 1 second to about 1 minute, about 30 seconds to about 30 minutes, about 1 minute to about 1 hour, about 30 minutes to about 3 hours, about 1 hours to about 5 hours, about 3 hours to about 10 hours, about 7 hours to about 18 hours, about 12 hours to about 1 day, or about 18 hours to about 3 days. Typically, increasing the duration that the raw coal is heated to the desired temperature can increase the amount of the one or more impurities are removed from the raw coal. However, the raw coal can exhibit a maximum duration where heating the raw coal for periods of time longer than the maximum duration will have little or no effect on the amount of the one or more impurities that are removed from the raw coal. In some cases, the beneficiation process can comprise heating the raw coal to a first desired temperature for a first duration followed by heating the raw coal to a second, higher desired temperature for a second duration. The first and second durations can be the same or different.

In an embodiment, the beneficiation process can include heating the raw coal in an atmosphere comprising a halogen gas which can facilitate removal of one or more of the impurities from the raw coal and prevent oxidation or other reactions with the raw coal. In some embodiments, the coal can be beneficiated by heating the raw coal in an atmosphere including hydrogen which can increase the hydrogen to carbon ratio. In such an embodiment, the hydrogen can be provided from an outside hydrogen source or from hydrogen that was collected in another stage of the method 100. In some embodiments, the coal can be beneficiated by heating the raw coal in an atmosphere that is substantially hydrogen free. In such an embodiment, the substantially hydrogen free atmosphere can decrease the hydrogen to carbon ratio.

In some embodiments, the coal can be beneficiated by heating the raw coal in an atmosphere including hydrogen which can increase the hydrogen to carbon ratio. In such an embodiment, the hydrogen can be provided from an outside hydrogen source or from hydrogen that was collected in another stage of the method 100. In some embodiments, the coal can be beneficiated by heating the raw coal in an atmosphere that is substantially hydrogen free. In such an embodiment, the substantially hydrogen free atmosphere can decrease the hydrogen to carbon ratio.

In some other embodiments, the coal can be beneficiated by heating the coal to a desired temperature in the presence of one or more catalyst compounds. In some cases, beneficiating the coal can comprise pyrolyzing the coal, for example in the presence of a catalyst. In some embodiments, the raw coal can be beneficiated at or near atmospheric pressure (e.g., 0.8 to about 1.2 atmospheres), though the raw coal can be beneficiated at higher or lower pressures.

In some embodiments, beneficiation can include subjecting the raw coal to a WRITECoal beneficiation process, as described, for example, in U.S. Pat. No. 9,181,509 which is hereby incorporate by reference in its entirety. In some other embodiments, the coal can be beneficiated by heating the coal to a desired temperature in the presence of one or more catalyst compounds. In some cases, beneficiating the coal can comprise pyrolyzing the coal, for example in the presence of a catalyst. In some cases, the coal can be beneficiated by the BenePlus System, as developed and licensed by LP Amina and as described, for example, in U.S. Patent Publication No. 2017/0198221 which is hereby incorporated by reference in its entirety.

The beneficiated coal can comprise a significantly reduced amount (e.g., at least 25 wt. %, at least 50 wt. %, at least 75 wt. %, at least 90 wt. %, at least 95 wt. %, or at least 99 wt. %) of at least one of mercury, cadmium, other heavy metals, water, any of the other impurities disclosed herein, or any other impurity that can be present in the raw coal. The amount of the impurities that are left in the beneficiated coal can depend on the temperature that the raw coal was heated, the duration that the raw coal was heated, the atmosphere that the raw coal was exposed to during the beneficiation process, the presence of catalysts, etc. For example, beneficiating the coal can reduce the amount of mercury in the coal by about at least about 70 wt. %, 75 wt. %, 80 wt. %, 85 wt. %, 90 wt. %, or 92 wt. % or more. In some cases, beneficiating the coal can reduce the water or moisture content of the coal to less than about 5 wt. %, 4 wt. %, 3 wt. %, 2 wt. %, or 1.5 wt. % or lower. In some cases, beneficiating the coal can remove one or more of hydrogen, sulfur, oxygen, arsenic, selenium, cadmium, or volatile matter from the coal. The amount of one or more of these elements in the coal can be reduced by about 25 wt. % to about 90 wt. %.

However, as previously discussed, it can be desirable for a desired amount of one or more impurities to remain in the beneficiated coal after being subjected to a beneficiation process. For example, the beneficiation process can remove a desired amount of impurities such that a predetermined amount of mercury, cadmium, selenium, alkali metals, heterogeneous elements, and/or another element can selectively remain in the beneficiated coal after processing. In some cases, the desired amount of impurity that can remain in the beneficiated coal can be useful in the subsequent formation of the carbon fiber or, optionally, the one or more additional advanced carbon materials. In some cases, the desired amount of the impurity that can remain in the beneficiated coal can be incorporated into the carbon fiber and, optionally, the one or more advanced carbon materials. For example, where the advanced carbon material comprises synthetic graphene, a desired amount of cadmium can remain in the beneficiated coal and can be incorporated into the synthetic graphene to thereby improve the electrical, mechanical, or chemical properties thereof.

In an embodiment, the beneficiation process can be configured to maintain at least some of any of the impurities disclosed herein at any of the concentrations disclosed herein in the beneficiated coal after block 120 (but before block 130).

In an embodiment, the beneficiation process can be configured to decrease the hydrogen to carbon ratio of the coal. For example, after the beneficiation process, the hydrogen to carbon ratio of beneficiated coal can less than about 0.8, such as in ranges of about 0.6 to about 0.7, about 0.65 to about 0.75, or about 0.7 to about 0.8.

In some embodiments, beneficiating the coal during act 120 can produce one or more byproducts, such as one or more byproducts that can be captured and used in later processing steps, that can be valuable in and of themselves, or that can be subjected to further processing or use in the method 100. For example, beneficiating the coal can produce or separate gases or coal liquid extracts from the raw coal. These gases and/or coal liquid extracts can be captured or separated during processing. For example, beneficiating the coal at block 120 can produce at least one of $H_2$, $CO_2$, CO, $CH_4$, $C_2H_4$, $C_3H_6$, or other hydrocarbon gases, which can be captured and subsequently utilized in block 130 or in other process steps. In some cases, beneficiating the coal can result in coal liquid extracts (e.g., toluene or benzene) which can be captured for subsequent use or processing. In some cases, the impurities removed from the coal by the beneficiation process at block 120 can be captured for subsequent use. For example, water removed from the coal by the beneficiation process can be capture and utilized in subsequent process steps. In some embodiments, beneficiating the coal can also produce a solid material known as ash or char. In some cases, this char can be subjected to further processing to form activated carbon.

At block 130 the beneficiated coal can be processed via the processing facility. In some embodiments, processing the beneficiated coal can include subjecting the beneficiated coal to a liquid extraction process, such as a pyrolysis process (e.g., a high temperature pyrolysis process or a mild temperature pyrolysis process). It is noted that other liquefaction processes can be used instead of or in conjunction with the pyrolysis process, such as using a direct liquefaction process (discussed in more detail with regard to FIG. 2), an indirect liquefaction process (discussed in more detail with regard to FIG. 3), membranes (e.g., discussed in more detail with regard to FIG. 4), an electric arc process, a super critical solvent extraction process, or an electromagnetic heating process. The liquid extraction process can convert the beneficiated coal into at least one of pitch, one or more gases, one or more coal liquid extracts, or char.

In an embodiment, the liquid extraction processes of block 130 can comprise pyrolyzing the beneficiated coal via the processing facility. Pyrolyzing the beneficiated coal to form carbon fibers can include heating the beneficiated coal to a desired temperature for a desired duration, with or without elevating the pressure applied to the beneficiated coal. At the elevated temperatures, some of the organic structures within the beneficiated coal begin to breakdown forming lower molecular weight pyrolytic fragments. Some of the lower molecular weight pyrolytic fragments can escape the beneficiated coal as light gases (e.g., hydrogen, methane, carbon dioxide, etc.). These light gases can be captured and/or reused as discussed in more detail below. However, some of the lower molecular weight pyrolytic fragments can recombine or depolymerize to form small ring aromatic structures (e.g., single ring aromatic structure). The small ring aromatic structure can undergo condensation reactions wherein the small aromatic ring structure join together to form larger ring aromatic structures (e.g., polyaromatic hydrocarbons). Examples of the condensation reactions includes at least one of ring condensation, ring fusion, dehydrogenation, or other condensation reactions that grow the small ring aromatic structure. The larger ring aromatic structures can comprise isotropic pitches, isotropic resins, other products that include aligned polyaromatic layers, liquid crystalline structure (e.g. anisotropic pitches or anisotropic resins), mesophase pitches, or mesophase resins.

In an example, pyrolyzing the beneficiated coal can comprise a high temperature pyrolysis process that includes heating the beneficiated coal to a temperature greater than about 1000° C. at atmospheric process. The high temperature pyrolysis process can form benzene compounds, phenol compounds, high value oil, or other compounds that are useful in the formation of carbon fibers. In an example, pyrolyzing the beneficiated coal can comprise a mild temperature pyrolysis process that includes heating the beneficiated coal to a temperature of about 400° C. to about 650° C. at atmospheric pressure. The mild temperature pyrolysis process is likely to form coke than the high temperature pyrolysis process which can facilitate the formation of the resins disclosed herein. In some cases, the coal can be heated at high pressure (e.g., a pressure greater than about 1 atmosphere) and in the presence of a solvent. For example, the beneficiated coal can be pyrolyzed in the presence of a $CO_2$ solvent which can be held in a supercritical state. In some cases, the beneficiated coal can be pyrolyzed in a hydrogen atmosphere (e.g., hydrogen provided from an outside hydrogen source or hydrogen collected during the method 100) to increase the hydrogen to carbon ratio of the beneficiated coal or pyrolyzed in a hydrogen free atmosphere to decrease the hydrogen to carbon ratio of the beneficiated coal. In an embodiment, the beneficiated coal can be pyrolyzed in a hydrogen atmosphere (e.g., hydrogen provided from an outside hydrogen source or hydrogen collected from another stop of the method 100) to increase the hydrogen to carbon ratio of the coal or pyrolyzed in a hydrogen free atmosphere to decrease the hydrogen to carbon ratio of the coal. In some cases, the beneficiated coal can be pyrolyzed by the MuSCL System developed by TerraPower described, for example, in U.S. Pat. No. 10,144,874 which is hereby incorporate by reference in its entirety. Additional examples of pyrolysis processes that can be used to process the beneficiated coal are described in U.S. Patent Application Publication No. 2017/0198221, U.S. Patent Application Publication No. 2018/0311657, and *The ENCOAL mild gasification project, a DOE Assessment*, DOE/NETL-2002/1171 (2002), the disclosure of each of which is incorporated herein, in its entirety, by this reference.

In some embodiments, the pyrolysis process can comprise exposing the beneficiated coal to electromagnetic radiation at a desired intensity and for a desired duration. For example, block 130 can comprise exposing the beneficiated coal to microwave and/or radiofrequency (RF) radiation for a desired duration as part of the pyrolysis process. In some cases, this pyrolysis process can result in the bulk of the beneficiated coal remaining below pyrolytic temperatures, while individual particles of coal can be subjected to temperatures greater than about 1200° F. In some cases, this pyrolysis process can also comprise methane activation and/or methylation of at least some of the carbon comprising the beneficiated coal. In some embodiments, the beneficiated coal can be pyrolyzed by the Wave Liquefaction process developed by H Quest Vanguard, Inc. as described, for example, in U.S. Patent Publication No. 2017/0080399 which is hereby incorporate by reference in its entirety. Additional examples of processes for processing coal by exposing the beneficiated coal to electromagnetic radiation are disclosed in U.S. Pat. No. 6,512,216 and U.S. Patent Application Publication No. 2017/0101584, the disclosures of each of which is incorporated herein, in its entirety, by this references. Further examples of processes for processing coal by exposing the beneficiated coal to electromagnetic radiation are disclosed in U.S. Patent Application Publication No. 2018/0311657, the disclosure of which was previously incorporated herein.

Block 130 can be configured to prevent or selectively maintain selected quantities of the one or more impurities in the pyrolyzed coal. For example, after block 130, the pitch can include any of the impurities disclosed herein at any of the concentrations disclosed herein.

In an embodiment, after block 130, the pyrolyzed can exhibit a hydrogen to carbon ratio of less than about 0.8, such as in ranges as less than about 0.1, less than about 0.2, about 0.1 to about 0.2, about 0.15 to about 0.25, about 0.2 to about 0.4, about 0.3 to about 0.5, about 0.4 to about 0.6, or about 0.5 to about 0.7.

At block 140, pitch and, optionally, one or more byproducts (e.g., at least one of one or more gases, one or more coal liquid extracts, or char) are processed (e.g., extracted to the pyrolyzed coal) via the processing facility. In an embodiment, block 140 can represent the result of at least one of block 120 or block 130, rather than a separate action or process step. In an embodiment, block 140 can be performed substantially simultaneously with at least one of block 120 or block 130. In an embodiment, block 140 can be performed after at least one of block 120 or block 130.

In an embodiment, block 140 can include adding one or more additives to the beneficiated coal. For example, one or more other gases or liquids can be used during block 140 to add one or more additives to the beneficiated coal. Examples of gases or liquids that can be used during block 104 include hydrogen containing gases, natural gases, $CO_2$, petroleum products, one or more materials or compounds that are produced during at least one of block 120 or block 130, or one or more materials or compounds that can be produced by or captured during previous iterations of method 100.

As previously discussed, the raw coal can include one or more impurities therein and blocks 120 and 130 can be configured to not remove at least some of the impurities such that the beneficiated or pyrolyzed coal includes at least some of the impurities. The presence of the one or more impurities in the beneficiated or pyrolyzed coal can make adding one or more additives to the beneficiated or pyrolyzed coal unnecessary or can reduce the amount of additives that are added to the beneficiated or pyrolyzed coal. As such, the presence of the one or more impurities in the beneficiated or pyrolyzed coal can make the method 100 more efficient than methods of forming carbon fibers from a non-coal source since the beneficiated or pyrolyzed coal can have less additives added thereto than the non-coal source.

In some embodiments, pitch can be produced via the processing facility at block 140. As used herein, pitch, also known as coal pitch, coal tar, or coal tar pitch, can refer to a mixture of one or more typically viscoelastic polymers as will be well understood by the skilled artisan. In some embodiments, the pitch produced at block 140 can be a direct result of processing the beneficiated coal at step 130. The pitch produced at block 140 can comprise one or more high molecular weight polymers. In some embodiments, the pitch can have a melting point of greater than about 650° F. In some embodiments, the pitch can have a melting point that is high enough that some of the pitch (e.g., portions of the pitch not used to form the carbon fiber) can be used in a carbon fiber spinning process without the need for a plasticizer.

In an embodiment, the pitch can comprise aromatic hydrocarbons, for example polycyclic aromatic hydrocarbons. In some cases, the pitch can comprise at least about 50 wt. % polycyclic aromatic hydrocarbons, at least about 60 wt. %, 70 wt. %, 80 wt. %, 90 wt. %, 95 wt. %, or 99 wt. % or greater of polycyclic aromatic hydrocarbons. In an embodiment, the pitch can comprise less than about 0.1 wt. % ash or other solid material, less than about 0.05 wt. % ash or solid material, or less than about 0.01 wt. % ash or solid material. In some cases, the pitch can have a flash point greater than about 230° F., greater than about 250° F., greater than about 300° F., or in ranges of about 230° F. to about 250° F., about 240° F. to about 275° F., about 250° F. to about 300° F., about 275° F. to about 350° F., or about 300° F. to about 400° F. In some cases, the pitch can have an API gravity of less than about 4, less than about 3, or less than about 2, or less than about 1.5. In some embodiments, the pitch produced by the method 100 is not coke pitch. That is, in some cases, the pitch produced at block 140 is not produced from coke or a coke-based material. In some embodiments, coke is not produced at any point during the method 100.

In some embodiments, the pitch can include any of the impurities disclosed herein at any of the concentrations disclosed herein.

In some embodiments, the pitch can have a hydrogen to carbon ratio of about of less than about 0.8, such as in ranges as less than about 0.1, less than about 0.2, about 0.1 to about 0.2, about 0.15 to about 0.25, about 0.2 to about 0.4, about 0.3 to about 0.5, about 0.4 to about 0.6, or about 0.5 to about 0.7.

In an embodiment, the pitch can be relatively free of one or more selected impurities, such as water, non-carbon atoms including sulfur or nitrogen, or material such as coal ash or char, one or more non-carbon atoms (e.g., one or more of mercury, selenium, cadmium, arsenic, alkali metals, oxygen, halogens, sulfur or nitrogen), or material such as coal ash or char. For example, the pitch can comprise less than about 0.2 wt. % water, less than about 0.1 wt. %, less than about 0.05 wt. %, or less than about 0.01 wt. % water or lower. In an embodiment, the pitch can include one or more selected impurities in the concentrations disclosed above.

In an embodiment, the method 100 can also include producing one or more byproducts during block 140. Examples of the byproducts that can be formed during the block 140 are disclosed in [cited the other related applications], the disclosure of each of which is incorporated herein, in its entirety, by this reference. For example, the byproducts produced during block 140 can include at least one of one or more gases, one or more coal liquid extract, or char. It is noted that the one or more byproducts can also be produced during at least one of block 120 or block 130 instead of or in addition to block 140.

The coal liquid extracts can refer to any material that is extracted or produced from raw coal or beneficiated coal that is liquid at or near normal temperature and pressure (about 68° F. and 1 atmosphere of pressure). The one or more coal liquid extracts can comprise one or more liquid hydrocarbons. For example, coal liquid extracts can comprise one or more of benzene, toluene, alkanes or paraffins, alkenes, C2 compounds, C3 compounds, C4 compounds, T compounds, halogen compounds, phenols, or other saturated or unsaturated hydrocarbons. In some embodiments, the coal liquid extracts can include any of the impurities disclosed herein at any of the concentrations disclosed herein.

Char, also known as ash, can refer to any solid material which remains after gases, coal extract liquids, and/or pitch have been removed from raw coal. Char can be produced during at least one of block 120, block 130, or block 140. In an example, the char can comprise a solid high surface area carbonaceous material. In an example, the char can have a relatively low hydrogen to carbon ratio, such as a hydrogen to carbon ratio that is lower than the hydrogen to carbon ratio of pitch produced at block 140. In some cases, char can have a hydrogen to carbon ratio of from about 0.05 to about 0.65. In an example, char can additionally comprise at least some pitch material, which can be referred to herein as intrinsic binder impregnation. In some cases, any residual pitch or other gaseous or liquid materials can be removed from the char prior to any subsequent processing of the char.

In some embodiments, the char can include any of the impurities disclosed herein at any of the concentrations disclosed herein. In some embodiments, the char can have a hydrogen to carbon ratio of less than about 0.7, such as in ranges as less than about 0.1, less than about 0.2, about 0.1 to about 0.2, about 0.15 to about 0.25, about 0.2 to about 0.4, about 0.3 to about 0.5, about 0.4 to about 0.6, or about 0.5 to about 0.7.

The gases can comprise hydrogen and/or carbon. For example, the gases can include $H_2$, $CO_2$, CO, $CH_4$, $C_2H_4$, $C_3H_6$, and/or other hydrocarbon gases. The gases can also include sulfur. In some cases, these gases can be at least one of captured, otherwise contained, or used during the processes described herein. In some embodiments at least 50%, at least 75%, at least 90%, 95%, or 99% of any gaseous or volatile byproducts of the method 100 can be captured. The gases captured during certain process steps can be used in subsequent process steps as described herein. In some cases, gases produced by and a captured as part of the processes described herein can be utilized by these same or subsequent processes in order to increase the efficiency and/or cost effectiveness of said processes. In some cases, the capture and reuse of byproducts can improve the efficiency and/or lower the cost of the method 100.

In an embodiment, the method 100 can include reacting captured hydrogen gas ($H_2$) with captured carbon dioxide ($CO_2$) (i.e., syngas) to form methane or another suitable gas or liquid thereby reducing the carbon footprint of the method 100. The captured hydrogen and carbon dioxide gas can be processed chemically (e.g., catalytically) to form monomeric compounds (e.g., olefins such as ethylene and/or propylene) that can then be polymerized into higher molecular weight resin compounds. In an example, reacting the hydrogen with the carbon dioxide can reduce the amount of carbon dioxide produced by the method 100 by about 1% to about 99%, such as by about 1% to about 25%, about 20% to about 40%, or about 25% to about 50%.

In an embodiment, the pitch and the byproducts are all produced at block 140. In an embodiment, at least one of the pitch and at least one of the byproducts can be produced at separate times or separate processing steps from one another. In an embodiment, the pitch and at least one of the byproducts are produced together by the process 100 and, in particular, during block 140. In such an embodiment, the method 100 can include separating these products before any further processing of each individual product can occur. For example, pitch and coal liquid extracts can be simultaneously produced as a result of block 130 and can need to be separated from one another, by any process now know or which can be developed in the future, before further processing of either pitch or coal liquid extracts occurs.

In an embodiment, the pitch produced during block 140 are not subjected to further processing or refinement to alter the chemical composition of the pitch before block 150. In an embodiment, the pitch produced during block 140 can be subjected to one or more processes which can alter the chemical composition thereof prior to block 150. In an example, undesired impurities that remain in the pitch after block 140 can be removed therefrom prior to block 150. In such an example, the undesirable impurities can include impurities that could not be removed during block 120 and block 130 or excessive amounts of at least one impurity that is selected to be present in the carbon fiber. In an example, the pitch can be subjected to one or more processes to increase or decrease the hydrogen to carbon ratio of the pitch. In an example, the pitch can be subjected to one or more processes to produce mesophase pitch or otherwise alter the composition or properties of the pitch. In an embodiment, the one or more byproducts can also be used to form the carbon fiber during block 150. In such an embodiment, the one or more byproducts can or may not be subjected to further processing or refinement to alter the chemical composition thereof before block 150 using any of the processes disclosed herein or any other suitable process.

At block 150, at least the pitch produced at block 140 can be treated via the processing facility to produce at least one of the carbon fibers disclosed herein. In an embodiment, the pitch can be treated to product at least one of the carbon fibers disclosed herein by spinning the pitch to form carbon fibers. In some cases, spinning the pitch to form carbon fibers can include any process known in the art or developed in the future to convert pitch to carbon fibers, or carbon filament. In some cases, the pitch can be heated to a desired temperature during the spinning process, such as to about 650° F. In some cases, forming the carbon fibers can comprise drawing, spinning, and heating the pitch to produce the carbon fibers. In some cases, forming the carbon fibers can comprise spinning filaments of the pitch, heating the pitch in air to a first temperature, and then heating the spun pitch in an inert atmosphere to a second, higher temperature to form carbon filament. In some cases, a plasticizer can be added to the pitch to aid in spinning the pitch, however in some other embodiments, plasticizer may not be added before spinning the pitch. In some embodiments, forming the carbon fibers can comprise treating the pitch to produce one or more of any of the advanced carbon materials described herein.

In an embodiment, block 150 can include adding one or more additives to the pitch or the carbon fiber if the pitch has already been treated to form the carbon fiber.

The carbon fibers formed during block 150 can include one or more impurities therein. The properties of the carbon fibers can depend, at least in part, on the one or more impurities that are present in the carbon fiber. In other words, the properties of the carbon fibers can be tunable via at least one of the addition, control, or removal of the impurities from the coal. For example, the properties of the carbon fibers that can depend on the presences of the one or more impurities can include at least one of elasticity (Young's modulus), tensile strength, failure mechanism, and the like. In an embodiment, the one or more impurities can include at least one impurity that was initially present in the raw coal thereby negating the need to add the at least one impurity into at least one of the raw coal, the beneficiated coal, the pitch, or the byproducts. In an embodiment, the one or more impurities can include at least one impurity that was added to at least one of the raw coal, the beneficiated coal, the pitch, or the byproducts.

In some embodiments, where the additional advanced carbon materials can comprise carbon fibers, the carbon fibers can have different or improved physical properties as compared to carbon fibers formed by conventional processes (e.g., carbon fibers produced by spinning polyacrylonitrile ("PAN")). The different or improved physical properties can be caused by the impurities that are present in the raw coal and that remain in the carbon fibers. In some cases, carbon fibers produced by the processes described herein can have a higher degree of molecular orientation along the fiber axis than carbon fibers produced from PAN. In some cases, carbon fibers produced by the processes described herein can have a higher elastic modulus than carbon fibers produced from PAN. In some cases, carbon fibers produced by the processes described herein can have a higher thermal and electrical conductivity than carbon fibers produced from PAN. However, in some embodiments, the additional advanced carbon materials can comprise PAN, and thus carbon fibers can be produced from PAN that is formed from coal according to the processes described herein.

In an embodiment, the carbon fibers can include any of the impurities disclosed herein at any of the concentrations disclosed herein.

In an embodiment, the hydrogen to carbon ratio of the resin can be about 0.7 to about 1.0, such as in ranges of about 0.7 to about 0.75, about 0.725 to about 0.0775, about 0.75 to about 0.8, about 0.0775 to about 0.85, about 0.8 to about 0.9, about 0.85 to about 0.95, or about 0.9 to about 1.0.

In an embodiment, the method 100 can include recycling carbon material (e.g., resin, pitch, etc.) exhibiting a hydrogen to carbon ratio that is greater than the desired hydrogen to carbon ratio, such as greater than about 0.2, greater than about 0.3, greater than about 0.4, greater than about 0.5, greater than about 0.6, or greater than about 0.7. For example, recycling the carbon material exhibiting a high hydrogen to carbon ratio can include adding the carbon material to the raw coal, the beneficiated coal, the pyrolyzed coal, the pitch before the pitch is processed, etc. Recycling the carbon material can increase the amount of resin or other advanced carbon material that is produced during the method 100.

As previously discussed, the beneficiated coal can be processed using a direct liquefaction process other than a pyrolysis process. The direct liquefaction process can include producing resins from coal under hydrogenation conditions to produce a naphtha which can further be "steam cracked" (e.g., converted into so-called "naphtha cracker") to produce light olefin products (e.g., ethylene and/or) propylene. One example of a direct liquefaction process includes the H-Coal process developed in the Catlettsburg refinery and by Shenhua of China to produce liquid transportation fuels, chemical intermediates, and naphtha.

Figure 2:
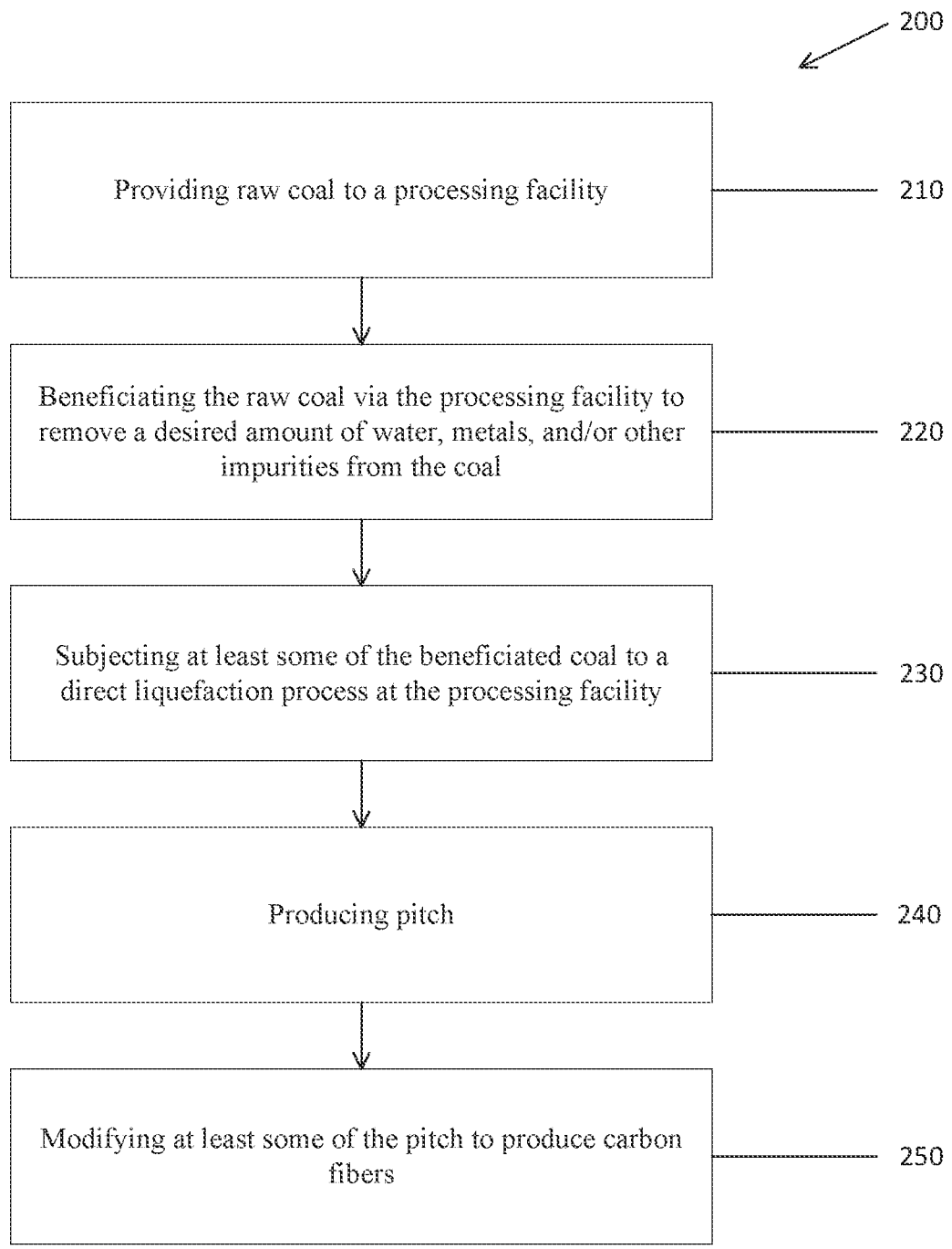
FIG. 2 is a flow chart of an example method 200 to form carbon fibers using a direct liquefaction process, according to an embodiment.

FIG. 2 is a flow chart of an example method 200 to form carbon fibers using a direct liquefaction process, according to an embodiment. Except as otherwise disclosed herein, the method 200 is the same or substantially similar to the method 100. The method 200 can include providing coal to a processing facility at block 210. The method 200 can also include beneficiating the coal via the processing facility at block 220 to remove a desired amount of water, metals, and/or other impurities from the coal. The method 200 can further includes subjecting at least some of the beneficiated coal to a direct liquefaction process at the processing facility at block 230. Additionally, the method 200 can include producing pitch at block 240. Also, the method 200 can include modifying the pitch to produce carbon fibers at block 250. The method 200 is only an example. As such, one or more blocks of the method 200 can be omitted, supplemented, combined, or divided. Further, the method 200 can include one or more additional acts.

Block 230 includes processing the beneficiated coal using a direct liquefaction process. The direct liquefaction process can include heating the beneficiated coal above a desired temperature (e.g., about 400° C. to about 500° C.) for a duration thereby converting the beneficiated coal into a liquid. In some cases, the beneficiated coal can be heated in the presence of one or more catalysts and/or at an elevated pressure. In some cases, the beneficiated coal can be heated in an atmosphere comprising $H_2$. In some cases, the direct liquefaction process can be a hydrogenation or hydrocracking process. In such cases, the direct liquefaction process can be performed in a hydrogen atmosphere. In some cases, a solvent can be added to the beneficiated coal during the direct liquefaction process. In some cases, the beneficiated coal can be subjected to a direct liquefaction process developed by Axens as described, for example, in U.S. Patent Publication No. 2017/0313886, which is hereby incorporated by reference in its entirety.

As previously discussed, the beneficiated coal can be processed using an indirect liquefaction process other than a pyrolysis process. The indirect liquefaction process can include producing resins from the raw coal in a high temperature gasification process to form so-called syngas (e.g., a mixture of hydrogen gas and at least one of carbon monoxide or carbon dioxide). The syngas can be processed chemically to form monomeric compounds that can then be polymerized into higher molecular weight resin compounds. For example, syngas can be converted into methanol which can be catalytically converted into light olefins (e.g., ethylene and/or propylene). Ethylene and/or propylene can be converted into carbon fibers. The light olefins formed during the indirect liquefaction process and/or the other process disclosed herein can also be precursors to other polymeric compounds. For example, the ammoxidation of propylene results in the formation of acrylonitrile monomers which can then be converted into polyacrylonitrile.

Figure 3:
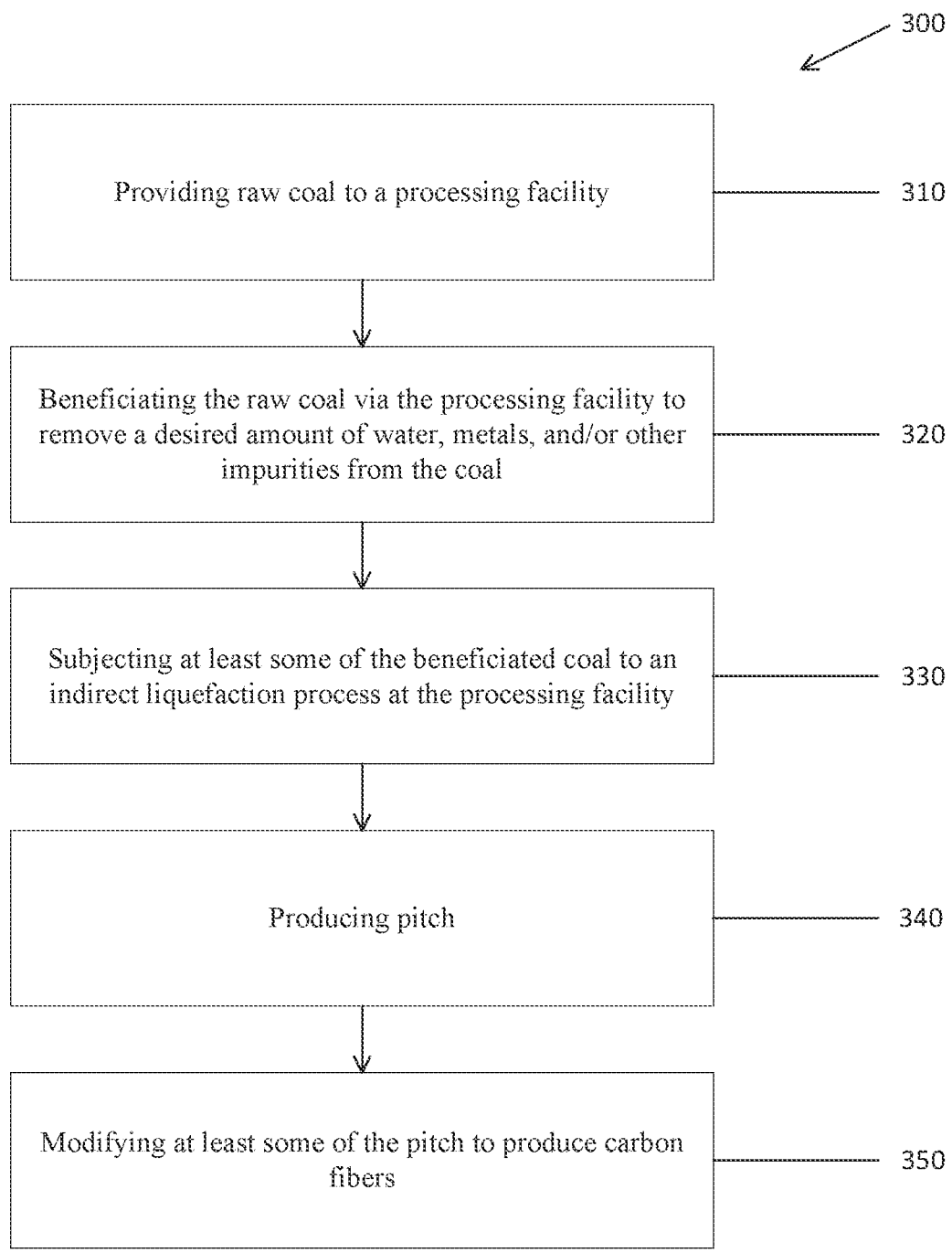
FIG. 3 is a flow chart of an example method 300 to form carbon fibers using an indirect liquefaction process, according to an embodiment.

FIG. 3 is a flow chart of an example method 300 to form carbon fibers using an indirect liquefaction process, according to an embodiment. Except as otherwise disclosed herein, the method 300 is the same or substantially similar to the method 100 and/or method 200. The method 300 can include providing coal to a processing facility at block 310. The method 300 can also include beneficiating the coal via the processing facility at block 320 to remove a desired amount of water, metals, and/or other impurities from the coal. The method 300 can further includes subjecting at least some of the beneficiated coal to an indirect liquefaction process at the processing facility at block 330. Additionally, the method 300 can include producing syngas or another coa-derived element (e.g., char, pitch, etc.) at block 340. Also, the method 300 can include modifying the pitch to produce carbon fibers at block 350. The method 300 is only an example. As such, one or more blocks of the method 300 can be omitted, supplemented, combined, or divided. Further, the method 300 can include one or more additional acts.

Block 330 includes processing the beneficiated coal using an indirect liquefaction process. The indirect liquefaction process can include converting the beneficiated coal to a gas or gases and then converting the gas or gases into one or more liquids. The one or more gases can include, but are not limited to, syngas (e.g., a mixture of $H_2$ and CO gas). In an example, the indirect liquefaction process can include heating the beneficiated coal to a desired temperature (e.g., about 1400° C. to about 1600° C.) for a desired duration at a desire pressure (e.g., about 40 bars to about 60 bars). In an example, the gases formed during the indirect liquefaction process can then be converted to liquids or other materials, such as ammonia or methanol. The gases formed during the indirect liquefaction process can be converted into liquids or other materials at a desired temperature (e.g., about 200° C. to about 350° C.) and at a desired pressure (e.g., about 10 bars to about 40 bars). The liquids or other material can then be subjected to further processing to produce hydrocarbons that can be formed into the carbon fibers, polymers that can be formed into the carbon fibers, other precursors of the carbon fibers, or the carbon fibers themselves. The hydrocarbon can include olefins (e.g., ethylene and propylene), aromatic hydrocarbons, toluene, benzene, paraxylene, or other hydrocarbons. In a particular example, the gases can be converted to olefins by a process developed by Honeywell UOP as described, for example, in U.S. Patent Publication No. 2015/0141726, which is hereby incorporated by reference in its entirety. In some cases, the beneficiated coal can be subjected to an indirect liquefaction process.

As previously discussed, the beneficiated coal can be processed using membranes instead of a pyrolysis process. Examples of using membranes to process coal include separating hydrogen from coal in gasification reactors using membranes. The membranes can include specialty ceramic materials, such as one or more advanced carbon-based materials (e.g., one or more graphene-based materials). The membranes can facilitate the separation of hydrogen from coal at relative low temperature and/or processing of slurry-based coal, both of which can decrease costs and improve the efficiency of the process of formin the one or more resins. Examples of using membranes to process the beneficiated coal are disclosed in V. Kyriakou, et al., *A protonic ceramic membrane reactor for the production of hydrogen from coal steam gasification*, 553 J. Membrane Sci. 163 (2018) and Francis C. Arrillaga, et al., *Coal to Hydrogen: A Novel Membrane Reactor for Direct Extraction*, GCEP Energy Workshops (2004), the disclosures of each of which are incorporated herein, in its entirety, by this reference.

Figure 4:
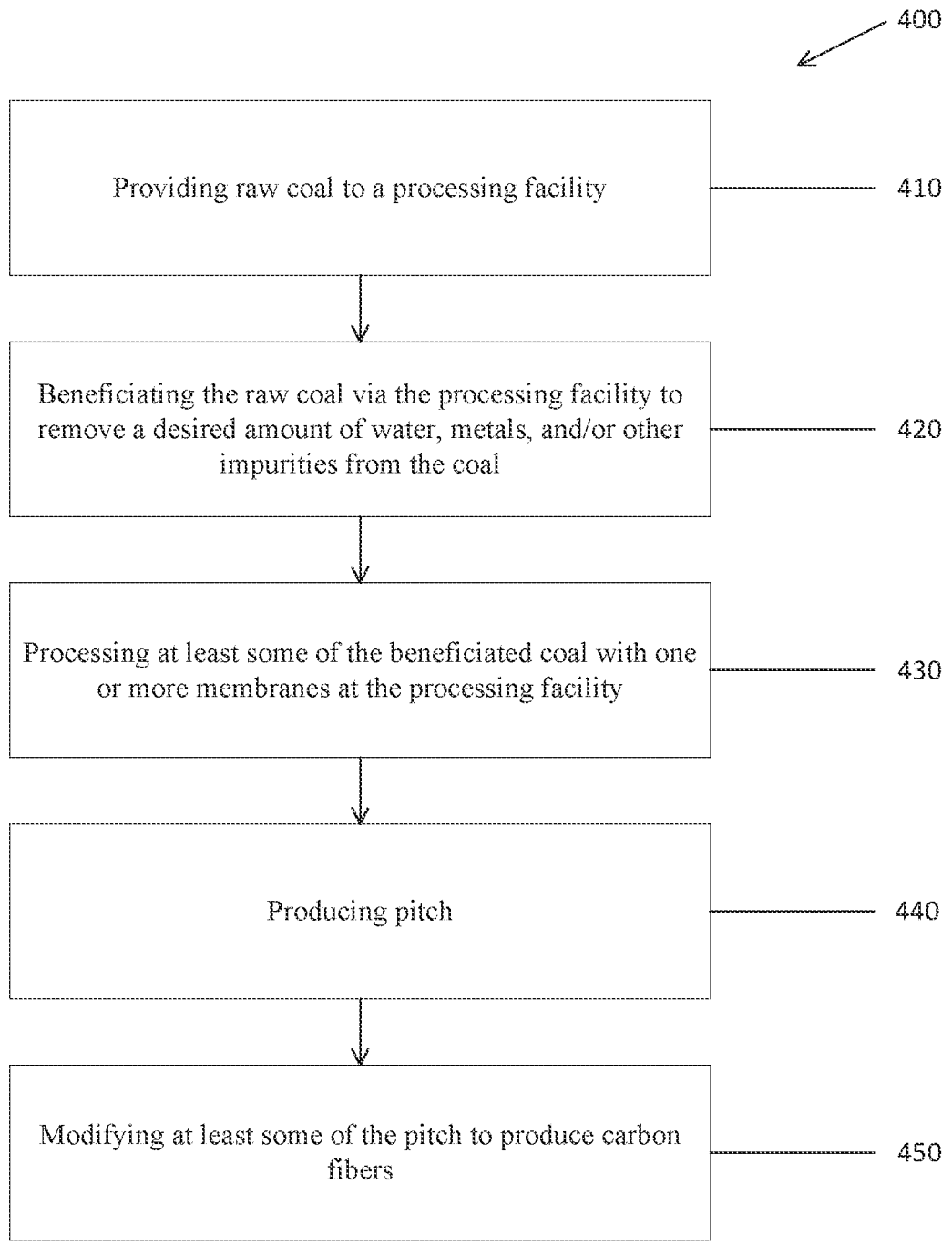
FIG. 4 is a flow chart of an example method 400 to form carbon fibers using one or more membranes, according to an embodiment.

FIG. 4 is a flow chart of an example method 400 to form carbon fibers using one or more membranes, according to an embodiment. Except as otherwise disclosed herein, the method 400 is the same as or substantially similar to the method 100, method 200, and/or the method 300. The method 400 can include providing coal to a processing facility at block 410. The method 400 can also include beneficiating the coal via the processing facility at block 420 to remove a desired amount of water, metals, and/or other impurities from the coal. The method 400 can further includes processing at least some of the beneficiated coal with one or more membranes at the processing facility at block 430. Additionally, the method 400 can include producing pitch at block 440. Also, the method 400 can include modifying the pitch to produce carbon fibers at block 450. The method 400 is only an example. As such, one or more blocks of the method 400 can be omitted, supplemented, combined, or divided. Further, the method 400 can include one or more additional acts.

Block 430 includes processing the beneficiated coal in the presence of one or more membranes. In some cases, these membranes can serve to at least one of physically separate, chemically separate, or crack the beneficiated coal to produce products therefrom. Examples of the membranes includes advanced carbon-based materials. In an embodiment, these products can be substantially similar to the products produced by the other liquefaction processes disclosed herein, but may not use the amount of heat or pressure that the other liquefaction process can require. Thus, processing beneficiated coal with one or more membranes can produce substantially similar products to a liquefaction process but can require substantially less energy to do so. In an embodiment, the one or more membranes can comprise various pore sizes, chemical properties, physical properties, or electrical properties to isolate desirable compounds and/or produce desirable compounds from the beneficiated coal.

The beneficiated coal can be processed using other process other than or in addition to the pyrolysis processes disclosed herein, the direct liquefaction processes disclosed herein, the indirect liquefaction processes disclosed herein, or the process disclosed herein that use membranes. In an example, the beneficiated coal can be processed using an electric arc process. In an example, the beneficiate coal can be processed using a super critical solvent extraction process. Examples of super critical solvent extraction processes that can be used to process the beneficiate coal are disclosed in Jonathan J. Kolak, *A Procedure for the Supercritical Fluid Extraction of Coal Samples, with Subsequent Analysis of Extracted Hydrocarbon*, USGS (2006) and Ye Sun et al., *Evaluation of Coal Extraction with Supercritical Carbon Dioxide/1-Methyl-2-pyrrolidone Mixed Solvent*

Figure 5:
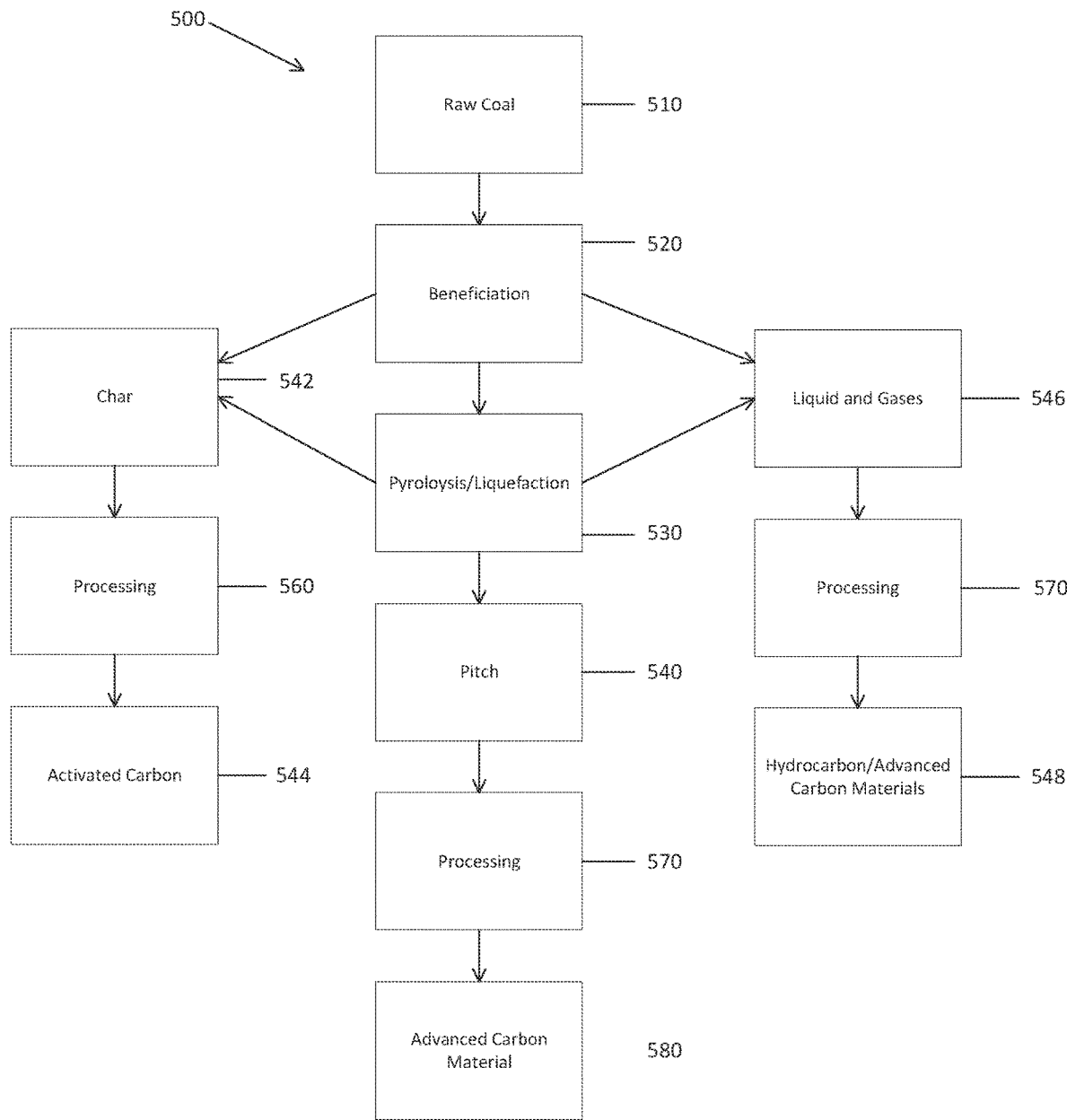
FIG. 5 illustrates a material flow diagram of an example of a method 500 of producing carbon fiber and, optionally, one or more advanced carbon materials from coal in accordance with the present disclosure, according to an embodiment.

FIG. 5 illustrates a material flow diagram of an example of a method 500 of producing carbon fiber and, optionally, one or more advanced carbon materials from coal in accordance with the present disclosure, according to an embodiment. Except as otherwise disclosed herein, the method 500 is the same as or substantially similar to any of the methods 100, 200, 300, or 400 of FIGS. 1-4. For example, the method 500 can be a combination of two or more of the methods 100, 200, 300, or 400 of FIGS. 1-4. At block 510, raw coal is provided to a processing facility, for example by a mining process, such as high wall mining. The raw coal can include any of the raw coal disclosed herein. The raw coal can then be subjected to a beneficiation process to remove a desired amount of water, metals, volatile matter, and other impurities as described herein at block 520. The beneficiation process can include any of the beneficiation processes disclosed herein. In some cases, the beneficiation process can produce byproducts, such as char (block 542) and gases and/or coal liquid extracts (546), in addition to the beneficiated coal. The beneficiated coal can be subjected to a liquid extraction process (e.g., pyrolysis, direct liquefaction, or indirect liquefaction process) at block 530 and as described herein to produce pitch (block 540). Again, in some cases, the pyrolysis or liquefaction process of block 540 can produce byproducts, such as char (block 542) and coal liquid extracts and gases (block 546). In some cases, the char 542 can be processed or treated at block 560 to produce an additional advanced carbon material, for example activated carbon (block 544), as described herein. In some cases, the coal liquid extract 546 can be processed or treated at block 570 to produce at least one of hydrocarbons (e.g., benzene and paraxylenes), carbon fibers, or other additional advanced carbon materials (block 548), as described herein. At block 550, the pitch can be processed or treated to produce carbon fibers (block 580), as described herein. In an embodiment, the block 580 can also include processing or treating the pitch to produce one or more additional advanced carbon materials in addition to the carbon fiber, as described herein.

In some embodiments, the method 500 can be entirely carried out at a single processing facility. However, in some other cases, one or more blocks can be carried out at different processing facilities and/or different locations. For example, char 542 or coal liquid extract 546 can be transported to a second location where blocks 560 and 570 can be carried out.

Although the processes described herein relate to the production of carbon-based carbon fibers and additional advanced carbon materials from coal, in some embodiments these processes can be utilized to produce silicon products, such as silicone carbon fibers. For example, in some embodiments, sand or other raw materials comprising silicon can be used in the processes and methods described herein to produce one or more silicone carbon fibers.

Figure 6:
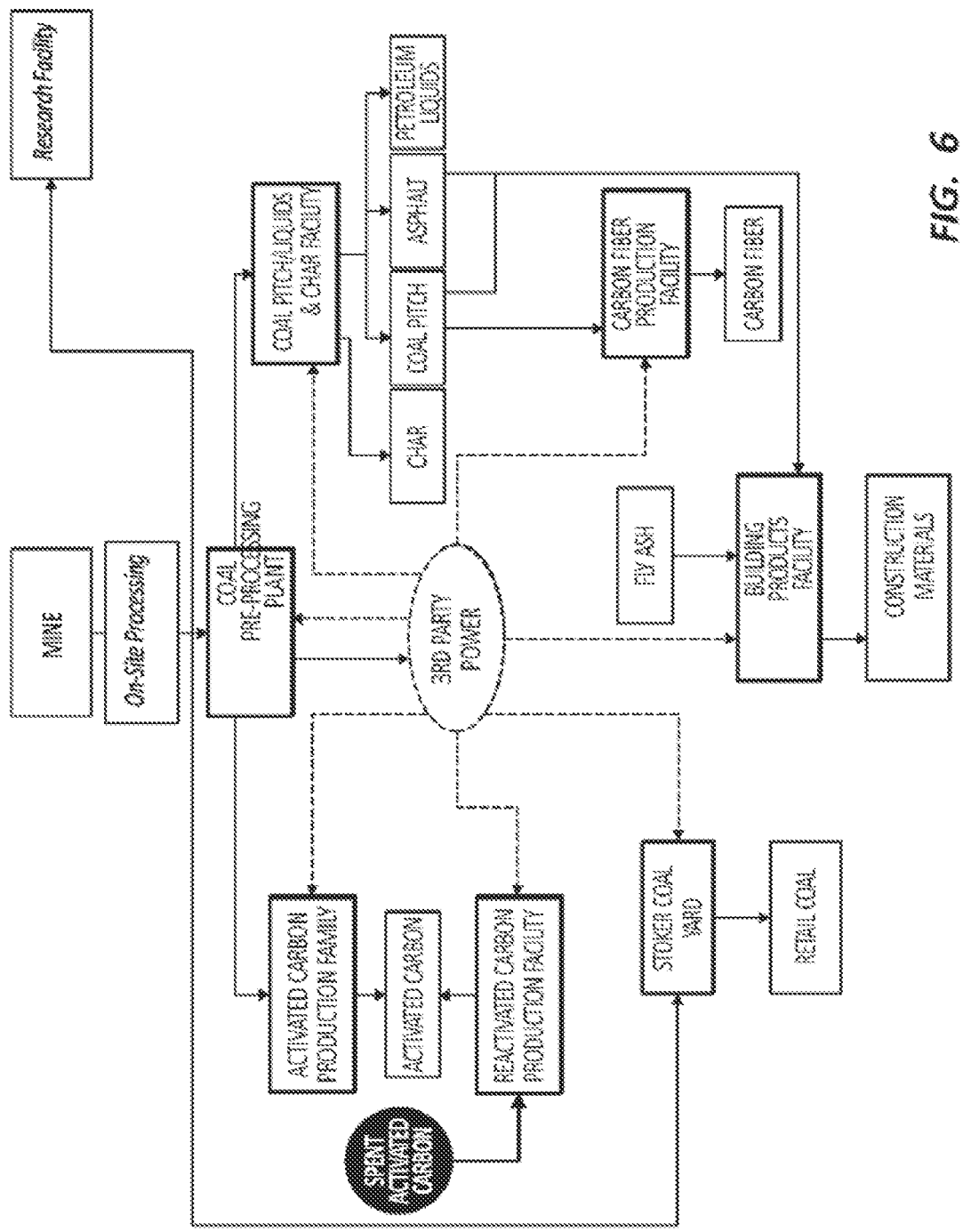
FIG. 6 is a diagram illustrating the flow of energy and coal in a processing facility for the production of one or more advanced carbon materials as described herein and according to some embodiments.

FIG. 6 is a diagram illustrating the flow of energy and coal in a processing facility for the production of one or more advanced carbon materials as described herein and according to some embodiments. As can be seen in FIG. 6, and as described herein, raw coal from a mine, such as the Brook Mine in Wyoming, can be processed to form carbon fiber and, optionally, one or more additional advanced carbon materials, such as construction materials, and/or activated carbon.

Figure 7:
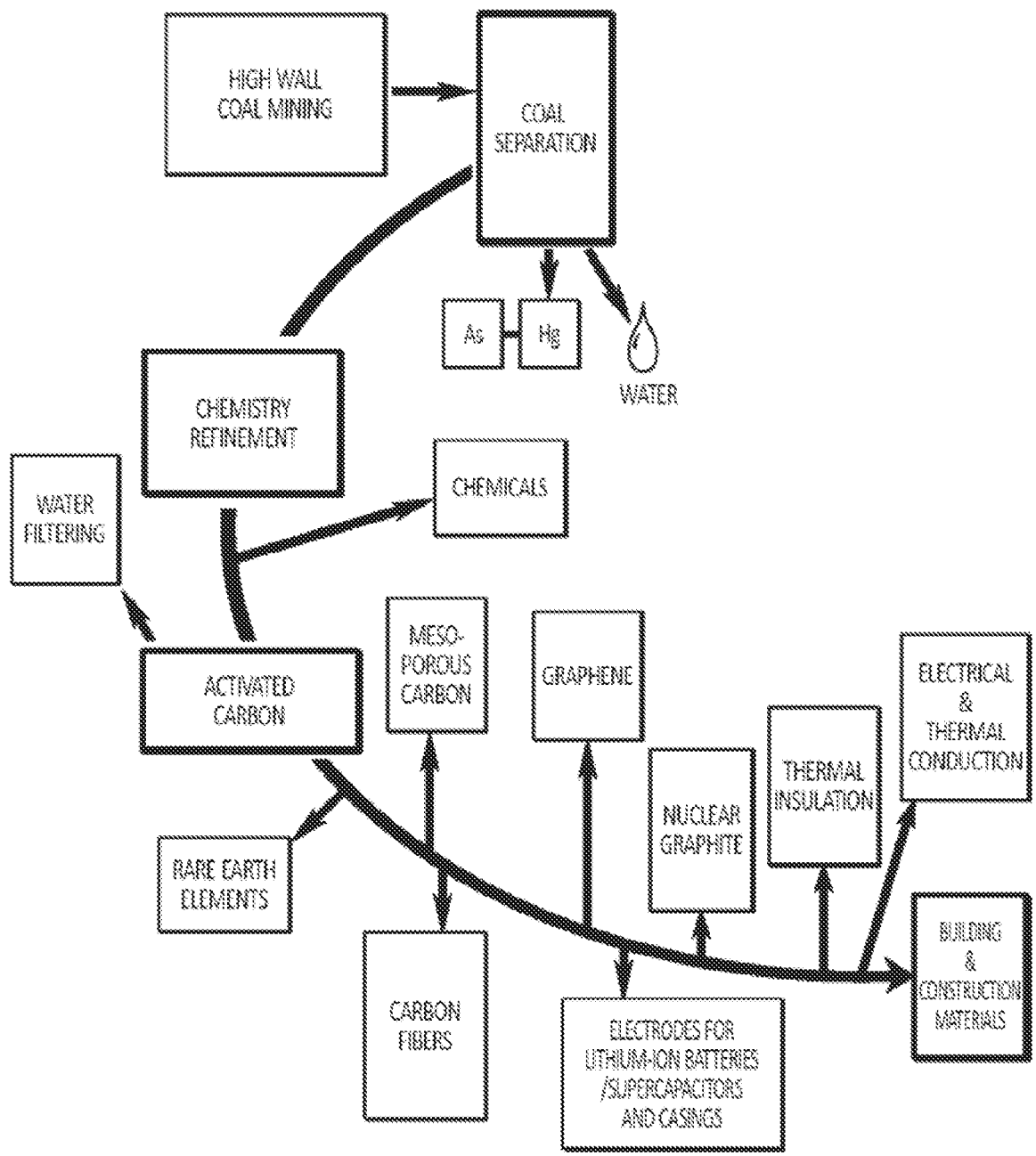
FIG. 7 is a diagram illustrating the process flow of raw coal, for example from a high wall coal mine, as it is processed according to the embodiments described herein to form various advanced carbon materials, such as activated carbon, graphene, materials for use in batteries, and building and construction materials, according to an embodiment.

FIG. 7 is a diagram illustrating the process flow of raw coal, for example from a high wall coal mine, as it is processed according to the embodiments described herein to form various advanced carbon materials, such as activated carbon, graphene, materials for use in batteries, and building and construction materials, according to an embodiment. As illustrated, and according to some embodiments, processing of the coal can produce advanced carbon materials which can themselves be subjected to further processing to form other advanced carbon materials. Further, in some embodiments, the byproducts from the production of advanced carbon materials can themselves be subjected to further processing to produce other advanced carbon materials as described herein.

Figure 8:
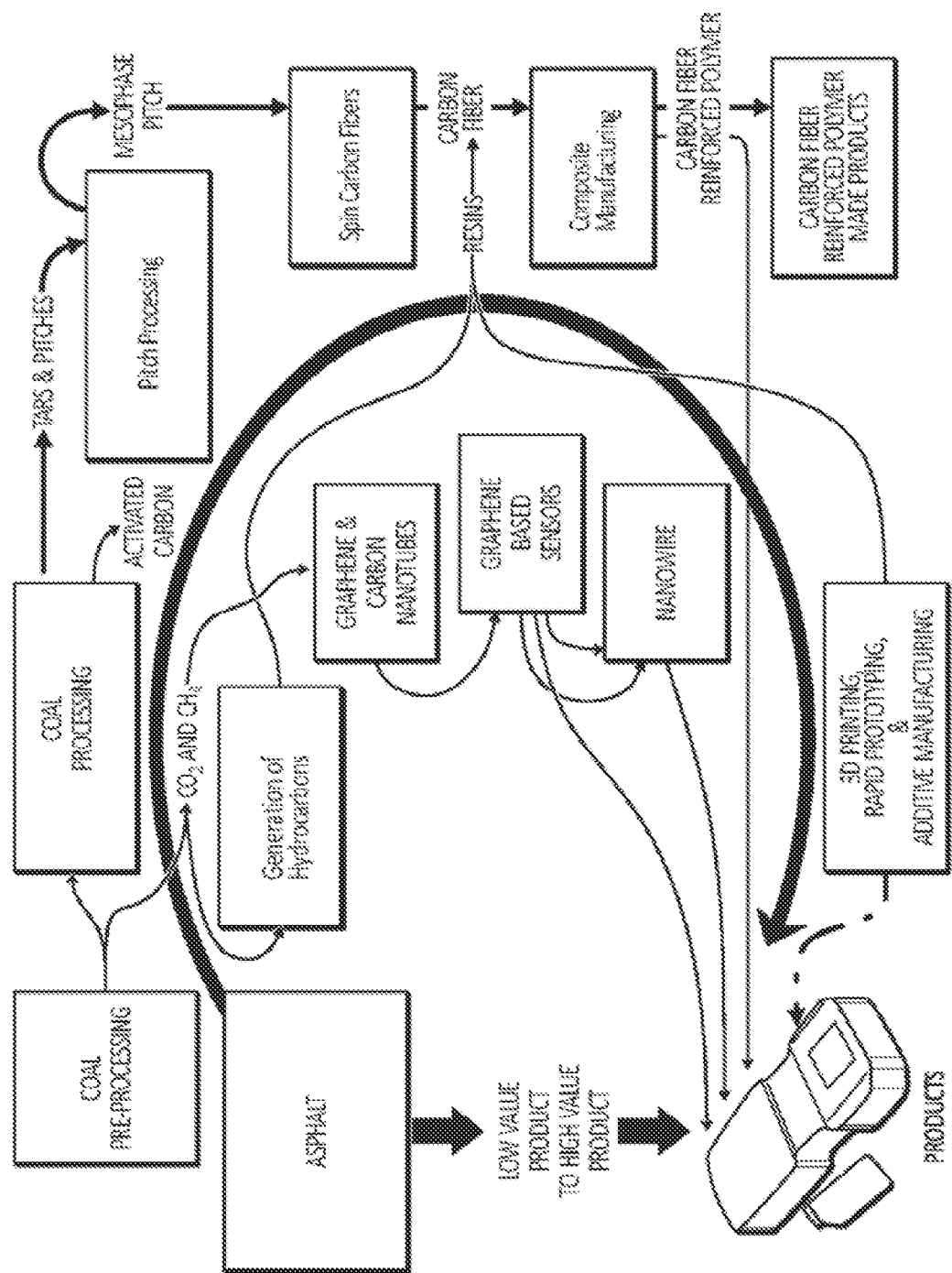
FIG. 8 is a diagram illustrating the process flow of raw coal to various advanced carbon materials according to the processes described herein, according to an embodiment.

FIG. 8 is a diagram illustrating the process flow of raw coal to various advanced carbon materials according to the processes described herein, according to an embodiment. FIG. 8 further illustrates how, according to some embodiments, the advanced carbon material produced according to the processes described herein can be utilized as one or more components in high-value finished products, such as automotive grade CFRP, or graphene based biosensors.

Applications of the Carbon Fibers

The carbon fibers produced during at least one of the methods 100, 200, 300, 400, or 500 can be configured to be used in a variety of applications and, optionally, these methods can include using the carbon fibers in one or more of these application. In an embodiment, the carbon fibers can be configured to be used in a carbon fiber reinforced composite. For example, the carbon fibers can be combined with at least one matrix material to form the carbon fiber reinforced composite by any process known in the art or that can be developed in the future. The matrix material can comprise at least one of a polymer (e.g., a resin made from coal), a metal, or a ceramic material. In some cases, the matrix can include any one of the additional advanced carbon materials disclosed herein. In some embodiments, the carbon fiber reinforced polymer can be formed into a desired structure. In some embodiments, the additional advanced carbon materials can be produced via the processes described herein and can be combined with one or more other materials via the processing facility to produce a composite material having a desired form.

In some embodiments, the carbon fiber reinforced composite can include metals or concrete including carbon fibers. In some examples, the carbon fiber reinforced composite can be 3D printed. In some examples, carbon fiber or the carbon fiber reinforced composites produced from coal as described herein can be used as rebar in concrete or can be used as other construction materials.

In an embodiment, the carbon fibers disclosed herein can be modified on site by a user in order to achieve the desired chemical or mechanical properties of the carbon fiber reinforced composite. In some cases, a first carbon fiber produced from coal by the processes described herein can be mixed with predetermined amount of a second carbon fiber that is different than the first carbon fibers. In an example, the first carbon fiber and the second carbon fibers are both formed from coal but exhibit different properties (e.g., the first and second carbon fibers include different impurities). In an example, the first carbon fiber is formed from coal while the second carbon fibers are formed from oil. The amount of the first and second carbon fibers can be selected based on the desired properties of the carbon fiber reinforced composite formed from the first and second carbon fibers. For example, where a user desires a higher young's modulus, they can be directed to add a predetermined amount of a first carbon fiber produced from coal in order to raise the young's modulus of the second carbon fiber formed from oil.

In some cases, an advanced carbon material such as carbon fibers, include activated carbon and/or can be functionalized and tuned as desired. In some cases, any of the advanced carbon materials or carbon fibers described herein can be functionalized or used to form functionalized products. For example, in some cases an advanced carbon material produced according to the methods described herein can be functionalized to adsorb one or more predetermined materials, elements, and/or substances from water, the atmosphere, or other mediums as desired. In some cases, advanced carbon material produced according to the methods described herein can adsorb one or more types of rare earth elements produced by coal processing plants, such as the processing facilities described herein. In some cases, advanced carbon material produced according to the methods described herein can adsorb one or more valuable predetermined elements or compounds from sea water. In some cases, advanced carbon material produced according to the methods described herein can adsorb $CO_2$ from the ambient atmosphere.

Additional Advanced Carbon Materials

As previously discussed, the methods and processes described herein can be used to produce carbon fiber and, optionally, one or more additional advanced carbon materials from coal. As used herein, the term additional advanced carbon materials can refer to one or more non-carbon fiber materials comprising carbon. The additional advanced carbon materials can be formed from at least one of the pitch (e.g., the portions of the pitch not used to form the carbon fiber) or one or more of the byproducts produced during the methods disclosed herein. In an example, the methods disclosed herein can be utilized to produce an amount of a carbon fiber and, subsequently, an amount of at least one additional advanced carbon material. In an example, the method 100 can be utilized to produce an amount of the carbon fiber and an amount of the at least one second advanced carbon material simultaneously, for instance, via parallel processing utilizing the methods disclosed herein. In some embodiments, the additional advanced carbon materials can be a resin, polymer, or other hydrocarbon material.

In an embodiment, the methods disclosed herein can include forming resin from the pitch or byproducts produced during the methods disclosed herein. For example, the resins formed from at least the pitch can include polyacrylonitrile, polyurethane resins, cyanate ester resins, epoxy resins, methacrylate resins, polyester resins, fused aromatic ring structures (e.g., polycyclic aromatic hydrocarbons), and other suitable resins. In an example, the resins formed according to the processes disclosed herein can include resins formed from resin precursors. Examples of resin precursors include C2 compounds (e.g., ethane, ethylene, acetylene, etc.), C3 compounds (e.g., propylene, cyclopropane, propene, etc.), C4 compounds (e.g., butadiene, butane, t-butanol, etc.), benzene compounds, toluene compounds, halogen compounds, phenols, or any other suitable resin precursor.

In an embodiment, the pitch can be treated to product at least one of the resins disclosed, for example, by forming the pitch into one or more organic compounds (e.g., olefins, other resin precursors, other polymers) and polymerizing the one or more organic compounds. In an embodiment, the coal liquid extracts can be treated at the processing facility to form at least one of the resins disclosed herein. In an embodiment, forming the resins disclosed herein can include adding one or more additives to the pitch, the byproducts, or the resin if the resin has already been formed. The additives added to the pitch, byproducts, or the resin can include one or more photo activators (e.g., one or more ultraviolet light activates) or one or more thermal activators.

In such an embodiment, the resin can be subjected to further processing via the processing facility to produce a polymer part or product. For example, the resin can be used to produce sheets, extrusion, three dimensional structures using a molding process, or another other suitable process. In an embodiment, the resins can be configured to produce carbon three dimensional ("3D") devices, such as via a 3D printing process. The 3D printing process can include forming the resin into meshes, hollow objects, solid objects, or other products. In some embodiments, a resin produced by the 3D printing processes described herein can be used in a continuous liquid interface production (CLIP) process as developed by Carbon3D, Inc. In an embodiments, the material properties of a 3D printed objected can be varied throughout the volume of the object by utilizing two or more resins produced form coal according to the processes described herein, where each of the two or more resins has different material properties when cured and/or each is activated by a different stimuluses. In an embodiment, the resins can be configured to be used in an additive manufacturing process.

In an embodiment, the methods disclosed herein can include processing at least one of the pitch or one or more of the byproducts to form synthetic graphite. In some cases, the synthetic graphite can be subjected to further processing to form synthetic graphene. For example, at least one of the pitch or one or more of the byproducts can be treated by exposure to heat, elevated pressure, and/or one or more catalysts to form synthetic graphite. As used herein, the term synthetic graphite is used to refer to any graphite material produced from a precursor material (e.g., any graphite material that does not occur naturally in the earth). In an embodiment, the methods disclosed herein can further comprise treating or processing the synthetic graphite, via the processing facility, to form synthetic graphene. As used herein, synthetic graphene refers to any graphene material produced or derived from synthetically formed graphite. For example, the synthetic graphite can be subjected to mechanical exfoliation to produce synthetic graphene. As described herein, a desired amount of one or more impurities can remain in the beneficiated coal and can thereby be incorporated into the synthetic graphene produced in order to adjust the chemical, electrical, and/or physical properties of the synthetic graphene.

In an embodiment, the methods disclosed herein can include subjecting any char produced during the methods to further processing to produce one or more additional advanced carbon material, such as activated carbon. In an example, processing the char can include carbonizing or heating the char (e.g., in a kiln). The char can then be activated via a physical activation process or a chemical activation process. Physical activation can comprise heating the char in an atmosphere comprising argon and/or nitrogen, or heating the char in an oxidizing atmosphere. Chemical activation can comprise impregnating the char with one or more chemicals, such as an acid, a base, or a salt. In some cases, chemical activation can further comprise carbonizing or heating the impregnated char to activate it. In some cases, chemical activation can require lower temperatures and less energy than physical activation. Further, in some cases, chemical byproducts produced by the method 100 can be utilized during the chemical activation process.

In some cases, the additional advanced carbon materials can comprise primarily carbon atoms. In some embodiments, the additional advanced carbon materials can comprise at least one carbon foams, or pyrolyzed carbon. In some embodiments, the additional advanced carbon materials can comprise one or more allotropes of carbon, such as any allotropes of carbon that are known in the art or that can be developed in the future. In some cases, the additional advanced carbon materials can comprise single-walled carbon nanotubes, multi-walled carbon nanotubes, carbon megatubes, carbon nanoribbons, carbon nanobuds, graphene, graphite nano-platelets, quantum dots, and fullerenes (e.g., buckminsterfullerene or multi-cored fullerenes).

In some cases, the additional advanced carbon materials can comprise elements in addition to carbon and can be, for example, a polymer or other hydrocarbon material. For example, the additional advanced carbon materials can comprise thermoset or thermoplastic polymers. In some cases, the additional advanced carbon materials can comprise a polyester, vinyl ester, or nylon polymer.

In some cases, the additional advanced carbon materials can comprise a biologically useful material or biopolymer. In other words, the additional advanced carbon materials can comprise a material including carbon that is at least one of used in biological systems or organisms, biocompatible, or is typically be produced by a biological organism. For example, the additional advanced carbon materials can be a protein, amino acid, nucleic acid, collagen, chitosan, sugar, or other biological material. In some cases, the additional advanced carbon materials can comprise a porous material, such as a membrane, for use in a biological and/or chemical process. For example, the additional advanced carbon materials can comprise perforated graphene.

Applications of the Additional Advanced Carbon Materials

The additional advanced carbon materials produced via the methods and processes described herein can be used in a wide variety of applications. In some cases, the additional advanced carbon materials produced via the processing facility described herein can be subjected to further processing to produce objects, devices, and other products from the additional advanced carbon materials. In other embodiments, the additional advanced carbon materials can be distributed to other production facilities for use. Importantly, in some embodiments, the processes described herein can produce two or more types of additional advanced carbon materials which can be combined at the processing facility into further products.

In such an embodiment, the resin can be subjected to further processing via the processing facility to produce a polymer part or product. For example, the resin can be used to produce sheets, extrusion, three dimensional structures using a molding process, or another other suitable process. In an embodiment, the resins can be configured to produce carbon three dimensional ("3D") devices, such as via a 3D printing process. The 3D printing process can include forming the resin into meshes, hollow objects, solid objects, or other products. In some embodiments, a resin produced by the 3D printing processes described herein can be used in a continuous liquid interface production (CLIP) process as developed by Carbon3D, Inc. In an embodiments, the material properties of a 3D printed objected can be varied throughout the volume of the object by utilizing two or more resins produced form coal according to the processes described herein, where each of the two or more resins has different material properties when cured and/or each is activated by a different stimuluses. In an embodiment, the resins can be configured to be used in an additive manufacturing process.

In some embodiments, a first additional advanced carbon material produced by the processes described herein can be used in a subsequent such process to produce a second, different additional advanced carbon material. For example, the first additional advanced carbon material can comprise molecular graphene membranes. The molecular graphene membranes can then be used in the processes described herein to chemically separate products of pyrolysis or liquefaction processes to produce carbon fibers. In some cases, this form of chemical separation via graphene membranes can be more thermally efficient than other separation processes that are typically employed. These carbon fibers in turn can be used in the CLIP process, for example to print a mesh.

In some embodiments where the additional advanced carbon materials comprise graphene, the graphene can be subjected to further treatment via the processing facility to form, for example, a graphene sensor. These graphene sensors can be used as disposable chips for detecting diseases via a handheld device. The graphene sensor can be able to immediately detect diseases, such as Lyme disease or the zika virus from a patient's blood, urine, saliva, or other bodily fluids or biological material, thereby eliminating any need to store blood samples for transportation to a lab. Further, the processes described herein can also be used to print the body of the hand-held device, and/or a consumable or attachment, such as a microfluidic chamber, for example via the CLIP process.

In some embodiments, additional advanced carbon materials produced by the processes described herein can be used in a wide variety of other applications. For example, the additional advanced carbon materials can comprise a carbon foam which can be used as an electrode in a lithium ion battery. In some cases, the additional advanced carbon materials can comprise activated carbon that can be used in an atmospheric $CO_2$ recapture process. In some cases, the atmospheric $CO_2$ recapture process can be carried out via the processing facility and captured $CO_2$ can be used in the processes described herein.

In some embodiments, additional advanced carbon materials, such as graphene, formed according to the processes described herein can be used to produce solar panels. In some cases these solar panels can have greater efficiencies than other conventionally produced solar panels. In some embodiments, additional advanced carbon materials formed according to the processes described herein can be used as precursors in electrospinning processes. For example, additional advanced carbon materials can be used to electrospin scaffolds or other structures having micron level resolution. In some cases the additional advanced carbon materials used in electrospinning can be biomaterials produced from coal according to the processes described herein. In some embodiments additional advanced carbon materials can be used to produce gels, for example medical grade gels such as hydrogels or silicone gels.

In some embodiments, one or more additional advanced carbon materials produced from coal according to the processes described herein can be used as automotive grade materials in the production of cars, trucks, or other automobiles. For example, carbon fiber reinforced composites including resins formed from coal can be used as automotive frames, structural components, body panels, engine blocks, and/or other components. In some cases, the components can be 3D printed and can be custom designed according to a user's preferences.

In some embodiments, one or more additional advanced carbon materials produced from coal according to the processes described herein can be used to form products for use in chemical or biological processes, such chromatography columns, membranes, and filters. In some cases, chromatography columns, membranes, and/or filters can be 3D printed from one or more additional advanced carbon materials produced from coal according to the processes described herein. In some cases, the chromatography columns, membranes, and/or filters can be used to isolate or remove antibodies, bacteria, parasites, and/or heavy metals from various solutions.

In some embodiments, one or more additional advanced carbon materials produced from coal according to the processes described herein can be used to form circuit boards. For example, a carbon foam produced from coal as described herein can be 3D printed to form a circuit board. In some cases a carbon foam circuit board can have superior electrical and thermal properties to typical printed circuit boards. In some embodiments, one or more additional advanced carbon materials produced from coal according to the processes described herein can be synthetic graphene and can be used in a variety of electronic applications, for example in forming quantum dots and in computer chips. In some cases, graphene can be used to produce biosensors that can be capable of isolating and/or identifying any number of biologically active molecules or substances, such as disease biomarkers or viruses.

Unless otherwise indicated, all numbers or expressions, such as those expressing dimensions, physical characteristics, etc., used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques. Further, the terms "have," "has," "having," "include," "includes," and "including" should be interpreted as being both open ended and closed end terms.

In addition, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

We claim:

1. A method of producing carbon fiber, comprising:
providing an amount of raw coal, the raw coal selected based on at least one of a destructive or non-destructive chemical analyzation technique, the raw coal including an impurity therein and having an initial hydrogen to carbon ratio greater than 0.7;
beneficiating the amount of raw coal to selectively remove at least some of the impurity comprising heteroatoms to form beneficiated coal;
processing the beneficiated coal to produce a pitch; and
modifying at least some of the pitch to produce the carbon fiber;
wherein the carbon fiber includes a selected amount of a remainder of the impurity.

2. The method of claim 1, wherein beneficiating the amount of raw coal includes removing at least 75 wt. % of at least one of mercury, arsenic, cadmium, water, or volatile compounds.

3. The method of claim 1, wherein processing the beneficiated coal includes pyrolyzing the beneficiated coal.

4. The method of claim 3, wherein pyrolyzing the beneficiated coal includes heating the beneficiated coal to about 400° C. to about 650° C. at atmospheric pressure.

5. The method of claim 1, wherein processing the beneficiated coal includes at least one of subjecting the beneficiated coal to a direct liquefaction process, subjecting the beneficiated coal to an indirect liquefaction, or using membranes.

6. The method of claim 1, further comprising capturing syngas.

7. The method of claim 1, wherein modifying at least some of the pitch to produce the carbon fiber includes modifying some of the pitch to produce the carbon fibers and a remainder of the pitch to form one or more additional advanced carbon materials.

8. The method of claim 7, wherein the one or more additional advanced carbon materials include a resin.

9. The method of claim 8, wherein modifying a remainder of the pitch to form one or more additional advanced carbon materials includes modifying the at least some of the pitch to form a resin precursor.

10. The method of claim 8, wherein the resin include at least one of polyethylene, polypropylene, polyacrylonitrile, polyurethane resins, cyanate ester resins, epoxy resins, methacrylate resins, polyester resins, or polycyclic aromatic hydrocarbons.

11. The method of claim 1, further comprising combining the carbon fibers with at least one matrix material to form the carbon fiber reinforced composite.

12. The method of claim 11, wherein the at least one matrix material includes a polymer.

13. The method of claim 11, wherein the at least one matrix material includes one or more of a metal or a ceramic.

14. A method of producing an advanced carbon material at a single processing facility, comprising:
providing an amount of raw coal to the single processing facility, the raw coal selected based on at least one of a destructive or non-destructive chemical analyzation technique and the raw coal including an impurity therein and having an initial hydrogen to carbon ratio greater than 0.7;
beneficiating the amount of raw coal at the single processing facility to selectively remove some of the impurity to form beneficiated coal;
processing the beneficiated coal at the single processing facility to produce a pitch; and
modifying at least some of the pitch at the single processing facility to produce a resin;
wherein the resin includes a selected amount of a remainder of the one or more impurities.

15. The method of claim 14, wherein beneficiating the amount of raw coal includes removing at least 75 wt. % of at least one of mercury, arsenic, cadmium, water, or volatile compounds.

16. The method of claim 4, wherein processing the beneficiated coal include pyrolyzing the beneficiated coal at a temperature of about 400° C. to about 650° C.

17. The method of claim 4, wherein processing the beneficiated coal includes at least one of subjecting the beneficiated coal to a direct liquefaction process, subjecting the beneficiated coal to an indirect liquefaction, or using membranes.

18. Carbon fiber formed from coal comprising a remainder of an impurity that was initially present in raw coal.

* * * * *